United States Patent
Maharajh et al.

(10) Patent No.: US 7,167,776 B2
(45) Date of Patent: Jan. 23, 2007

(54) METHOD AND SYSTEM FOR CONTROLLING A VAPOR GENERATOR

(75) Inventors: Niranjan Maharajh, Richmond, VA (US); Chris Tucker, Midlothian, VA (US); David Keeler, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 240 days.

(21) Appl. No.: 10/932,257

(22) Filed: Sep. 2, 2004

(65) Prior Publication Data

US 2006/0047368 A1 Mar. 2, 2006

(51) Int. Cl.
G05B 21/00 (2006.01)

(52) U.S. Cl. .................... 700/266; 392/394; 219/483; 219/497

(58) Field of Classification Search ............... 700/266, 700/282, 283, 299; 75/331, 355, 370; 128/200.11–200.23; 123/203.12, 203.26; 392/394, 480, 482, 392/484, 488; 219/483, 486, 497, 501, 505; 122/242; 264/5, 9, 12; 307/153; 315/300

See application file for complete search history.

(56) References Cited

U.S. PATENT DOCUMENTS

| | | | |
|---|---|---|---|
| 3,903,883 | A | 9/1975 | Pecina et al. |
| 4,027,145 | A | 5/1977 | McDonald et al. |
| 4,682,010 | A | 7/1987 | Drapeau et al. |
| 4,735,217 | A | 4/1988 | Gerth et al. |
| 4,922,901 | A | 5/1990 | Brooks et al. |
| 5,298,744 | A | 3/1994 | Mimura et al. |
| 5,474,059 | A | 12/1995 | Cooper |
| 5,743,251 | A | 4/1998 | Howell et al. |
| 6,173,207 | B1 | 1/2001 | Eidson |
| 6,196,219 | B1 | 3/2001 | Hess et al. |
| 6,205,362 | B1 | 3/2001 | Eidson |
| 6,212,670 | B1 | 4/2001 | Kaviani |
| 6,234,167 | B1 | 5/2001 | Cox et al. |

(Continued)

FOREIGN PATENT DOCUMENTS

EP 0 358 114 3/1990

(Continued)

OTHER PUBLICATIONS

U.S.P. Advisory Panel, "Recommendations of the USP on Aerosols on the USP General Chapters on Aerosols (601) and Uniformity of Dosage Units (905)", *Pharmocopeial Forum*, (May-Jun. 1994). pp. 7477 et seq., vol. 20, No. 3.

(Continued)

*Primary Examiner*—Leo Picard
*Assistant Examiner*—Sheela S. Rao
(74) *Attorney, Agent, or Firm*—Buchanan Ingersoll & Rooney PC

(57) ABSTRACT

A programmable vapor generator forms a volatilized liquid by supplying a material in liquid form to a flow passage and heating the flow passage, such that the material volatilizes and expands out of an outlet of the channel. The volatilized material, if desired, mixes with ambient air such that volatilized material condenses to form the aerosol. An apparatus and method for generating such a volatilized liquid, as well as the control and methods of heating, are disclosed as an analytical tool useful for experimental use, a tool useful for production of commercial products or an inhaler device.

36 Claims, 9 Drawing Sheets

U.S. PATENT DOCUMENTS

| | | |
|---|---|---|
| 6,246,389 B1 | 6/2001 | Timm |
| 6,264,613 B1 | 7/2001 | Pfeiffer et al. |
| 6,269,267 B1 | 7/2001 | Bardy et al. |
| 6,463,347 B1 | 10/2002 | Nevruz et al. |
| 6,501,052 B2 | 12/2002 | Cox et al. |
| 6,528,018 B1 | 3/2003 | Berndt |
| 6,568,390 B2 | 5/2003 | Nichols et al. |
| 6,766,220 B2 | 7/2004 | McRae et al. |
| 6,868,368 B1 | 3/2005 | Lang |
| 2002/0079309 A1 | 6/2002 | Cox et al. |
| 2003/0132219 A1 | 7/2003 | Cox et al. |

FOREIGN PATENT DOCUMENTS

| | | |
|---|---|---|
| GB | 1103992 | 2/1968 |
| WO | WO 94/09842 | 5/1994 |
| WO | WO 02/051466 | 7/2002 |
| WO | WO 02/051467 | 7/2002 |
| WO | WO 02/051468 | 7/2002 |
| WO | WO 02/051469 | 7/2002 |
| WO | WO 02/051551 | 7/2002 |

OTHER PUBLICATIONS

Yasuo Kousaka et al., "Generation of Aerosol Particles by Boiling of Suspensions", *Aerosol Science and Technology*, (1994), pp. 236-240, vol. 21.

Michael Hindle et al., "High Efficiency Fine Particle Generation Using Novel Condensation Technology", *Respiratory Drug Delivery VI*, (1998), pp. 97-101, Aerosol Research Group, School of Pharmacy, Virginia Commonwealth University, Richmond, VA.

Written Opinion for PCT/US02/23994 dated Jul. 31, 2003.

Notification of Transmittal of the International Search Report or the Declaration for PCT/US02/23994 dated Jan. 2, 2003.

Makansi, J., "Plants Gain Confidence in Optimization Software", Power, McGraw-Hill Company, New York, NY, U.S., vol. 142, No. 5, Sep. 1998, pp. 59-60, 62 and 64, XP000784359, ISSN: 0032-5929.

International Search Report and Written Opinion dated Aug. 10, 2006 for PCT/US2005/030955.

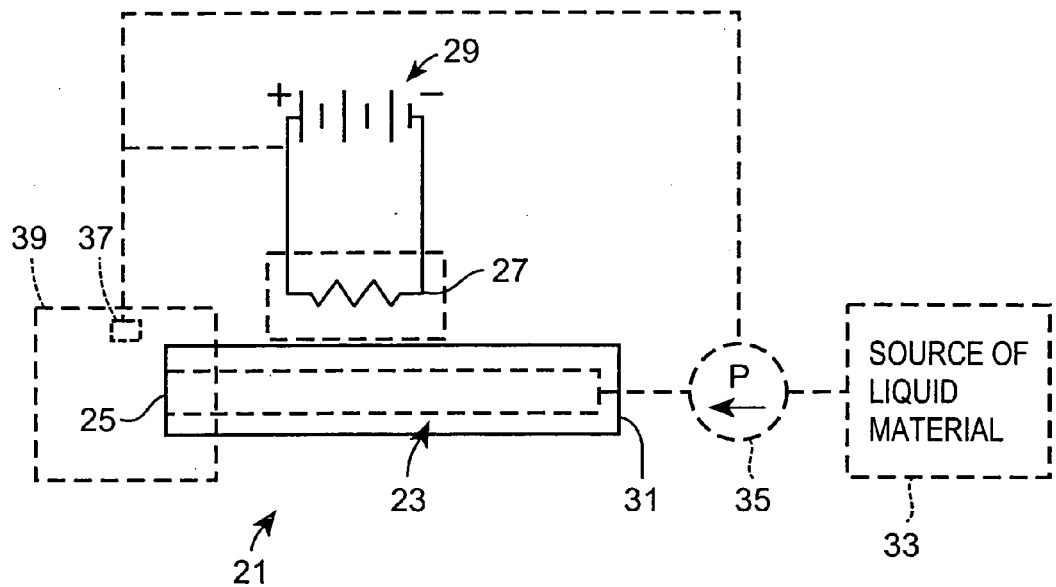
Prior Art  FIG. 1
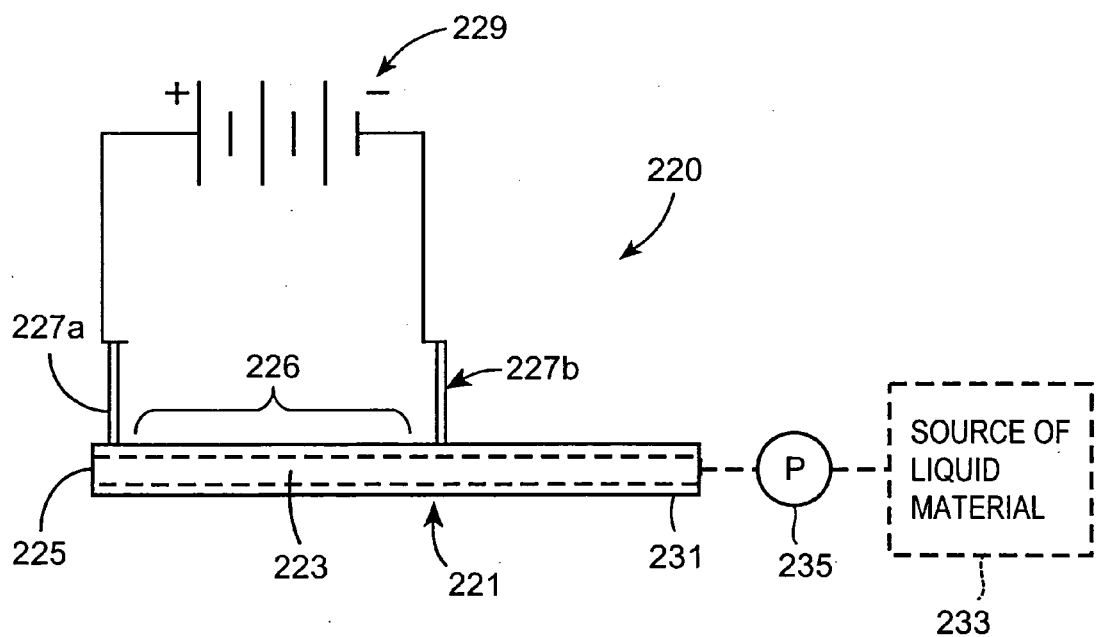
FIG. 2

METHOD AND SYSTEM FOR CONTROLLING A VAPOR GENERATOR

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights, whatsoever.

BACKGROUND OF THE INVENTION

1. Field of the Invention

The invention relates generally to a flexible platform that generates aerosols and vapors through the volatilization of a liquid for laboratory testing and development of applications for volatilized liquids.

2. Description of Related Art

U.S. Pat. No. 5,743,251, which is incorporated herein by reference, discloses an aerosol generator that includes a tube having a first open end. The aerosol generator further includes a heater for heating the tube to a temperature sufficient to volatilize material in a liquid form in the tube such that the volatilized material expands out of the open end of the tube and mixes with ambient air to form an aerosol.

An aerosol generator 21 according to U.S. Pat. No. 5,743,251 is schematically shown with reference to FIG. 1. The aerosol generator 21 includes a tube 23 having an open end 25. A heater 27 is positioned adjacent to at least a portion of the tube 23, but preferably in a way that provides a heated zone around the tube that maximizes heat transfer evenly throughout the heated zone. The heater 27 is connected to a power supply 29, preferably a DC power supply, such as a battery.

In operation, a material (not shown) in liquid form is introduced to the tube 23. The heater 27 heats the portion of the tube 23 to a sufficient temperature to volatilize the liquid material. In the case of an organic liquid material, the heater preferably heats the liquid material just to the boiling point of the liquid material, and preferably maintains the surface temperature of the tube 23 below 400 C, as most organic materials are not stable when they are exposed to temperatures above that temperature for periods of time. The volatilized material expands out of the open end 25 of the tube 23. The volatilized material mixes with ambient air outside of the tube and condenses to form particles, thereby forming an aerosol.

The tube 23 is a capillary tube or a portion thereof having an inside diameter of between 0.05 and 0.53 millimeter and the inside diameter of the tube can be approximately 0.1 millimeter. The tube 23 can be a portion of a fused silica capillary column, an aluminum silicate ceramic tube, or other substantially non-reactive materials capable of withstanding repeated heating cycles and generated pressures and having suitable heat conduction properties. If desired or necessary, an inside wall of the tube 23 may be provided with a coating for reducing the tendency of material to stick to the wall of the tube, which may result in clogging.

The tube 23 may be closed at a second end 31 and material in liquid form may be introduced into the tube 23 through the open end 25 when it is desired to form an aerosol. Thus, when the liquid material is heated by the heater 27, the volatilized material is only able to expand by exiting the tube 23 through the open end 25. However, the second end 31 of the tube is connected to a source 33 (shown by dotted lines in FIG. 1) of liquid material. The liquid material in the portion of the tube 23 volatilized by the heater 27 is prevented from expanding in the direction of the second end 31 of the tube, and is forced out of the open end 25 of the tube, as a result of back pressure of liquid from the source 33 of liquid material. The back pressure of the liquid is between about 20 to 300psi.

It is contemplated that a variety of uses can be developed for the aerosol generator described above. In order to investigate such uses, it would be desirable to have an instrument capable of generating vapors and aerosols to be evaluated. It would be further desirable to establish operational profiles for controlling the instrument, thereby simplifying the operation of the instrument across a range of operating parameters and conditions.

SUMMARY OF THE INVENTION

The invention provides a programmable instrument for volatilizing liquid material, thus facilitating investigational use of the vaporized liquid for various applications.

Exemplary embodiments are directed toward a method and system for controlling operation of a vapor generator, including (a) receiving vapor generator control parameters; (b) directing the operation of the vapor generator for a fixed period, wherein the generator is controlled by the received control parameters; (c) storing the control parameters and operational data of the vapor generator as a control profile for the vapor generator; (d) repeating steps (b)–(c) for a predetermined number of iterations; (e) selecting a stored control profile; and (f) automatically controlling the operation of the vapor generator with the data of the selected control profile.

A material in liquid form is supplied to a flow passage and the liquid material is heated to a temperature sufficient to volatilize the material such that the material expands out of the flow passage, which results in a vapor of the volatilized material, the volatilized material, then if desired, condensing upon mixing with air to form an aerosol. A programmable controller is used to control delivery of liquid material to the flow passage and/or control heating of a heater arrangement for volatilizing the liquid.

An embodiment is directed towards an instrument and method for generating an aerosol with a flow passage defined by a metal tube capable of conducting electricity. The tube has a first open end and a power supply for supplying power to a heater comprises a section of the metal tube such that the tube heats to a temperature sufficient to volatilize the liquid material in the flow passage. The volatilized material expands out of the open end of the flow passage and then may mix with ambient air to form an aerosol.

Another embodiment is directed towards an instrument and method for generating a volatilized liquid comprising a flow passage having a first open end and a heater which heats the flow passage to a temperature sufficient to volatilize material in liquid form such that the volatilized material expands out of the open end of the flow passage. The volatilized material may then mix with ambient air to form an aerosol. A controller is operable to maintain the temperature of the flow passage and regulate the flow of material. The controller is preferably capable of accepting manually entered commands or programs associated with operating parameters of the instrument. In addition, the controller is configured to be programmed for different parameters associated with the generation of the aerosol and/or precursor vapor, such that the controller can be used for developmental testing.

A further embodiment is directed to an instrument and method for generating a volatilized liquid including a flow passage with a first open end and a plurality of heaters for heating the flow passage to a temperature sufficient to volatilize material in liquid form in the flow passage such that the volatilized material expands out of the open end and may mix with ambient air to form an aerosol.

A method for generating an aerosol or vapor comprises steps of setting a target parameter, such as resistance of a heater arrangement, such as a resistance heater, corresponding to a temperature sufficient to volatilize a liquid material within a flow passage heated by the heater; supplying a liquid material to the flow passage; periodically determining the parameter of the heater; comparing the parameter to the target parameter; and energizing the heater when the parameter is less than the target parameter. In other embodiments, the method comprises setting a series or range of target parameters (i.e., multiple or variable target parameters), such as a series or range of resistance values of a heater.

Another embodiment is directed to an instrument for generation of volatilized material, which comprises at least one flow passage having an open end; a liquid supply operable to supply liquid material to the flow passage; at least one heater adapted to heat the flow passage to a temperature sufficient to volatilize material in liquid form in the flow passage such that the volatilized material expands out of the open end of the flow passage, the volatilized material optionally being admixed with air to form an aerosol; a first flow path in fluid communication with the open end of the flow passage; a second flow path in fluid communication with the open end of the flow passage, the second flow path being different from the first flow path; a first valve in fluid communication with the open end of the flow passage; and a controller operable to monitor a condition of the heater and to control operation of the first valve such that the volatilized material or aerosol (i) flows through the first flow path when the heater is in a non-conforming condition and (ii) flows through the second flow path when the heater is in a confirming condition.

BRIEF DESCRIPTION OF THE DRAWINGS

The features and advantages of the invention are well understood by reading the following detailed description in conjunction with the drawings in which:

FIG. 1 is a schematic view of an aerosol generator according to the prior art.

FIG. 2 shows an embodiment of an instrument wherein a section of a metal tube is used as a heater.

FIG. 10 shows a flow diagram for creating one or more profiles for controlling the operation of a vapor generator.

FIG. 11 shows a flow diagram of the automatic operation of a vapor generator based on a selected profile.

DETAILED DESCRIPTION OF PREFERRED EMBODIMENTS

Figure 3:
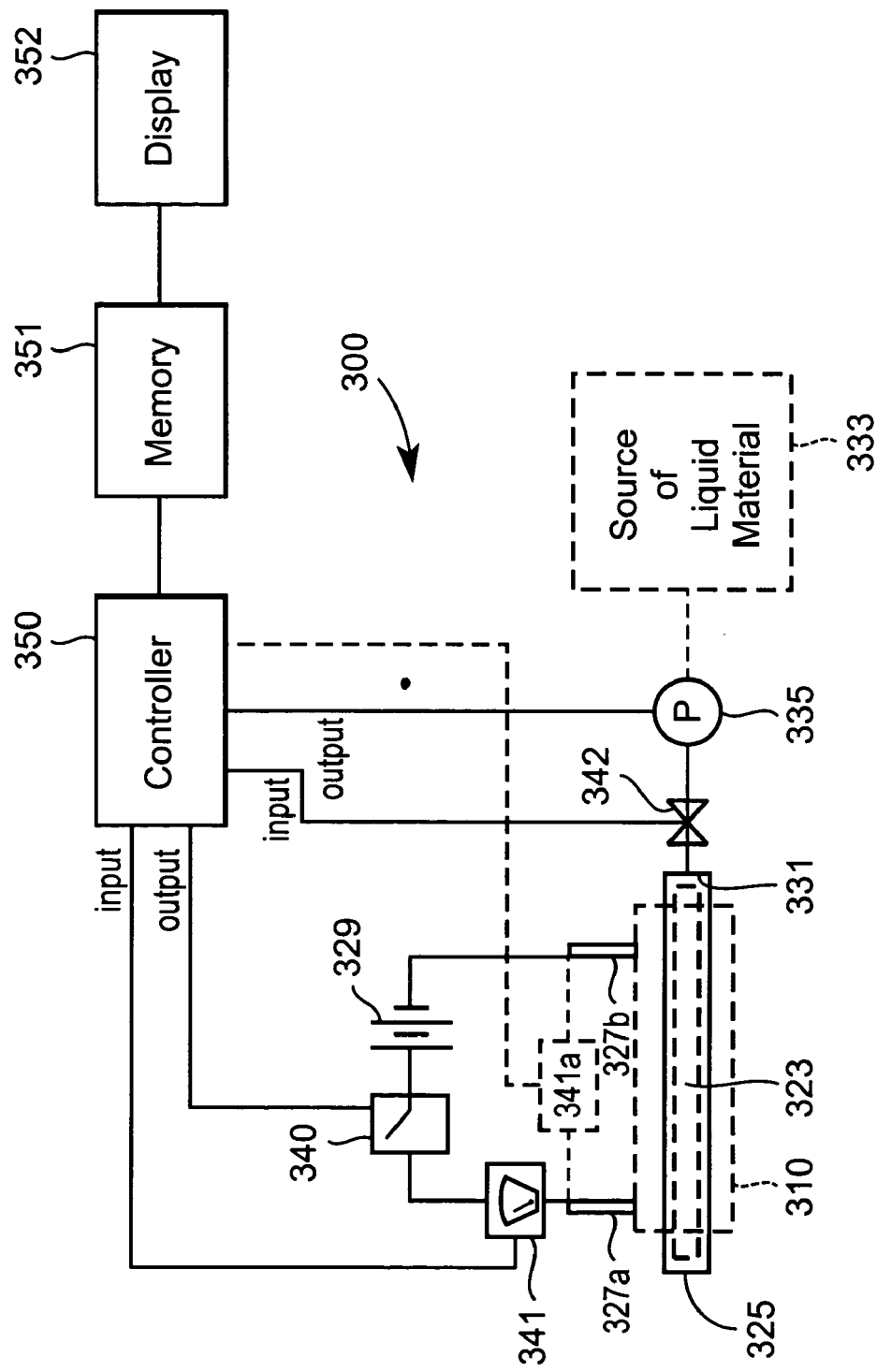
FIG. 3 shows an embodiment of an instrument wherein a controller operates a fluid supply and heater arrangement.

The invention provides an instrument, which incorporates control and measurement capabilities during generation of vaporized liquid, which may be condensed in ambient air to form an aerosol. The instrument can be used for medical, agricultural, industrial and scientific purposes. The instrument incorporates a heater arrangement which is used to volatilize liquid material. The instrument permits the precise application of energy to the heater arrangement under various control schemes to thereby generate solid and liquid aerosols. The aerosols can be produced from a single flow passage or a multiple flow passage arrangement.

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. Aerosols are also used for purposes such as providing desired scents to rooms, applying scents on the skin, and delivering paint and lubricant. Aerosols have also been considered for fuel delivery systems for high performance engines and turbines where the small particle size influences ignition rates, combustion efficiencies and flame speed. Aerosol generation in areas of combustion initially result in the formation of aerosols, but may after ignition result in only producing vapor, due to the temperature experienced at combustion.

Aerosols and the precursor vapor may also have applications in creating nano particles and other powders. The volatilization of liquid metals brings the possibility of producing micro ball bearings, foam metal and metal plating in a precise and cost effective manner. The uses of aerosols and the precursor vapor also have applications in the area of lubrication, where disbursement of the lubricant can be facilitated with the introduction of a concentration of particles of lubricant.

Development of such applications can be investigated using a versatile platform capable of producing an aerosol precursor vapor with a variety of user control elements, programmable functions and recording systems not presently available. The instrument can be used for such investigational purposes or used for commercial production of products formed as a result of, or in conjunction with, aerosol or volatilization of one or more materials.

The instrument incorporates a programmable vapor generator as described above. Embodiments of the instrument can incorporate various electronic hardware and software designed to achieve desired objectives. For instance, the instrument can be used to control and measure the energy applied to generate the vapor on time scales of one hundred milliseconds or less. The instrument can be programmed to control vapor generation by a variety of control strategies and using a variety of different vapor generator designs. Some of the control strategies include: constant and variable power profiles, constant and variable energy profiles, constant and variable heater resistance (temperature) profiles, constant and variable fluid flow profiles, constant and variable fluid pressure profiles, constant and variable voltage profiles, constant and variable current profiles, fluid valving control to the vapor generator, hot fluid heat transfer control, active energy control, inductive heating, different heater designs, multiple zone heaters, multiple heaters, and the like. Further control strategies can include variable, stepped heater resistance profiles, such as by varying the resistance parameter over time using one or more predetermined functions and/or equations. Other control strategies that can be used include constant and variable duty cycle profiles.

Exemplary software embodiments for controlling a vapor generator can be viewed as a plurality of modules that are utilized for controlling operation of the controller, receiving control parameters, creating generator control profiles, interfacing users with the generator control process, and controlling operation of heaters. The various software modules can be viewed as the means by which a programmed controller directs the operation of a vapor generator. The electronic hardware of the programmable controller can include a computer with one or more processors for controlling the operation of a vapor generator.

It is contemplated that the instrument can be used for characterization of aerosols for the delivery of medication to the lungs, characterization of aerosols for laboratory experiments, characterization of aerosols for inhalation studies, characterization of aerosols for the application of pesticides, characterization of vapors used in combustion applications, and the like. However, the instrument can be used for commercial production of products if so desired.

The liquid can be delivered to the heater arrangement by various techniques. For instance, a syringe pump can be used to deliver liquid to the heater arrangement in which case the liquid can be delivered at a constant rate for a predetermined time. However, if desired, the syringe pump can be used to deliver liquid to the heater arrangement at a variable rate. A programmed controller can execute the instructions for operating the syringe pump to deliver a desired amount of liquid to the heater arrangement. Another possibility is the use of a liquid pump, which withdraws liquid from a container and delivers the liquid at a constant rate to the heater arrangement. However, if desired, the liquid pump can deliver the liquid at a variable rate to the heater arrangement. With such an arrangement, the pump would continuously circulate the liquid and a valve would be used to divert the liquid to the heater arrangement as instructed by the controller. A further possibility is the use of a pressurized fluid arrangement wherein a valve is used to deliver the pressurized liquid to the heater arrangement as instructed by the controller.

The heater arrangement can be designed as a replaceable unit. For instance, the instrument can be designed to accommodate interchangeable heater arrangements wherein the size of the flow passage can be varied with respect to length and/or width thereof. Likewise, the heater used to volatilize liquid in the flow passage can take various forms such as a single heater or multiple heater arrangement.

Preferably, the flow passage is a capillary sized flow passage with transverse dimensions of 0.01 to 10 mm, preferably 0.05 to 1 mm, and more preferably about 0.1 to 0.5 mm. Alternatively, the capillary passage can be defined by transverse cross sectional area of the passage, which can be $8 \times 10^{-5}$ to 80 mm$^2$, preferably $2 \times 10^{-3}$ to $8 \times 10^{-1}$ mm$^2$ and more preferably $8 \times 10^{-3}$ to $2 \times 10^{-1}$ mm$^2$. As an example, the heater arrangement can comprise a stainless steel tube having electrical leads attached thereto for passage of DC current through the tube. The stainless steel tube can have any desired diameter. For investigating the behavior of aerosolized fluids including medication for inhalation, the tube can comprise various hypodermic needle gauges. A 32 gauge needle has an internal diameter of 0.11 mm (0.004 inch) and a 26 gauge needle has an internal diameter of 0.26 mm (0.01 inch). Thus, if a higher flow rate of liquid is desired, a larger sized flow passage can be used to volatilize the liquid. Although a stainless steel tube can be used as a combination heater/flow passage, other arrangements can be used for the flow passage/heater arrangement. For instance, a ceramic layer can be etched to provide a groove, which defines the flow passage and the ceramic layer can be overlaid with another ceramic layer, which incorporates a heater, such as a platinum heater, arranged to heat liquid in the groove. Like the stainless steel tube, the resistance heater can be heated by passing DC current therethrough.

In a preferred embodiment, the capillary includes a constriction at the outlet end of the flow passage. Further details of the constricted outlet are discussed in U.S. Patent Application No. 60/564,591, filed Apr. 23, 2004 and assigned to the same assignee of the present application, the contents of which are incorporated herein by reference.

The instrument can be programmed to achieve various control schemes. For instance, a resistance control scheme can be used to minimize overheating and under heating of the heater arrangement. In particular, a program can be used to send power to the heater until a target resistance value is reached. Under a power control scheme, a certain amount of power is supplied to the heater arrangement and the power is monitored and adjusted to maintain the heater arrangement at a desired temperature. In a voltage control scheme, a certain voltage (e.g., 4 volts) can be continuously supplied to the heater arrangement and a program (e.g., algorithm) is used to monitor and maintain the resistance at a target value. As an example, the controller can be programmed to control delivery of a pulse of power (e.g., duty cycle of 25% to 100% using a fixed pulse and pulse width of 1 to 10 msec) to the heater, measure the voltage drop across the heater, calculate the temperature dependent resistance of the heater and control the on/off supply of energy to the heater arrangement to maintain a target resistance value of the heater arrangement. In a preferred arrangement, the on time of the duty cycle is 2 to 4 milliseconds and the off time is varied between 2 and 16 milliseconds.

The instrument can be operated in conjunction with various detectors for analyzing the volatilized fluid. For instance, a filter can be used to collect aerosol and the collected aerosol can be weighed or submitted to gas or liquid chromatography for further evaluation. In order to determine particle sizing and distribution, a collection device can be located close to the jet of atomized liquid produced by the heater arrangement, or a manifold can be used to confine the aerosol and direct the aerosol to the collection device. Another possibility is to use a device which passes light through the aerosol to measure how thick the aerosol is and thus measure concentration of the particles in the aerosol. The instrument can be used to study the effects of vaporizing various hydrocarbon fuels such as jet fuel, gasoline, diesel, kerosene or the like. Another possibility is to use the instrument for studying pesticide application, e.g., the heater arrangement can be used to produce a fine fog or coarse spray for fumigating plants. The instrument can be used for toxicology studies wherein laboratory animals such as rats can be used to observe the effects of inhaled material.

The controller can be programmed to plot or store values of interest during operation of the heater arrangement. For instance, a memory can be used to store time and other parameters, which vary over time, such as resistance of the heater, total energy sent to the heater, power, voltage and/or current. The memory can also be used to store duty cycle and/or time to reach steady state. Further, such parameters can be plotted on a screen or printed out during operation of the heater arrangement or at a later time. The memory can also comprise a computer-readable medium encoded with software for controlling the operation of a vapor generator.

The instrument can be designed to produce a plurality of vaporized liquids. For instance, a conduit or manifold can be arranged to receive the aerosolized output of multiple heater arrangements. For example, two or more heater arrangements can be arranged along the axial length of a tube and the flow passages of the heater arrangements can be oriented to deliver the vaporized fluid in a direction perpendicular to the axis of the tube, or the directions of the vaporized liquid can be non-perpendicular to the tube axis. The multiple heater arrangements can be spaced apart axially along the length of the tube, or spaced apart circumferentially around the outer diameter of the tube.

The controller can be operated by a user interface, which allows selection of various programmable variables to be input into memory for operation of the instrument. The controller can be programmed to utilize an algorithm which performs calculations based on the following variables. Any suitable algorithm can be used to achieve the desired control scheme, e.g., algorithms provided with commercial diagnostic equipment available from Agilent Technologies, Inc., Palo Alto, Calif. See, for example, U.S. Pat. Nos. 6,269,267; 6,173,207; 6,246,613 and 6,205,362. An "event" variable switches the program between waiting to run (event=0) and running the heater (event=1). An event "trigger" variable activates a counter for sensing a trigger signal. A "pulse" variable corresponds to the output state for sending power to the heater (pulse=1). In a preferred embodiment, a "pulse count" variable activates a counter for an 8 millisecond heater cycle. An "event count" variable corresponds to the cumulative time in milliseconds during a run. A "resist target" variable corresponds to the target resistance for the heater during operation. An "energy" variable is the cumulative energy sent to the heater. A "resistance" variable is the measured resistance of the heater. An "energy COEF" variable corresponds to the calibration coefficiency for energy. A "resist COEF" variable is the calibration coefficient for resistance. An "armed" variable indicates which kind of trigger will be used to start the run. A "time" variable is the length of time for a run defined as the time the heater is powered and expressed in milliseconds. A "vd count" variable actuates a counter for timing the valve or energy delay. A "valve delay" variable can be used to open the valve after the heater is activated, the valve delay being the time lag in milliseconds between applying power to the heater and opening the valve. A "heater delay" variable can be used to open the valve before the heater is activated, the heater delay being the time lag in milliseconds between opening the valve and applying power to the heater.

FIG. 2 shows an embodiment of volatilized liquid generator 220. The volatilized liquid generator includes a member 221 defining a flow passage or channel 223 capable of conducting a fluid or vapor to a first open end 225 and a power supply 229 for applying a voltage to the member 221 such that a current in the member heats the channel to a temperature sufficient to volatilize a liquid material in the flow passage 223, such that the volatilized material expands out of the open end 225 of the flow passage 223 and, if desired, mixes with the ambient air to form an aerosol. Liquid can be supplied from a source of material by a pump 235 or other suitable mechanism.

The flow passage 223 in this embodiment is preferably 304 stainless steel. However, any electrically conductive material capable of being resistively heated, retaining the necessary structural integrity at the operating temperature experienced by the flow passage 223, and sufficiently non-reactive with the liquid material, could be used. Such materials include, but are not limited to copper, aluminum, metal composites, or other metals and alloys. The flow passage 223 has an open end 225 that allows the heated material to escape and an end 231 that allows the liquid material to be supplied.

The power supply for applying a voltage in this embodiment includes a voltage source 229 and two terminals 227a and 227b. The voltage source 229 can be a direct current battery. However, the use of alternating current could also be effective. The terminals 227a and 227b are preferably in contact with at least a portion of the perimeter of the member 221. The contact terminals 227a and 227b are preferably made of a material with a low resistance compared to the member 221 and have a coefficient of thermal expansion that avoids separation from the member 221.

The member 221 is preferably heated by resistance heating. The energy transferred to the member 221 from the voltage source 229 is governed by Ohm's Law.

$$V(\text{voltage}) = I(\text{current}) * R(\text{resistance}) \tag{1}$$

$$\text{Power} = V*I = V^2/R \tag{2}$$

In an example, for a 0.001 to 0.020 inch internal diameter/ 0.018 to 0.030 inch outside diameter tube of 304 stainless steel with an average internal resistance of about 3.12 ohms (for this example assuming the resistance remains constant for all temperatures) and the voltage source supplying 2.5 volts DC, the rate of energy transfer to the flow passage 223 is as follows:

$$\text{Power} = (2.5 \text{ V})^2/(3.12 \text{ ohm}) = 19.5 \text{ joules/sec} \tag{3}$$

Thus, the heat generated in the tube is a function of V (voltage drop across the flow passage) and the average resistance R of the tube.

A volatilized liquid generator, consistent with the foregoing example has been found to operate successfully in generating a vapor from liquid propylene glycol, when operated continuously at approximately 2.5 Volts and 0.8 Amps. The power supplied by the voltage source operating at this level is close to the minimal power requirements for volatilizing propylene glycol at a rate of 1.5 milligrams per second at atmospheric pressure, illustrating that the volatilized liquid generator 220 may be operated efficiently.

The volatilized liquid generator 220 may be operated intermittently, e.g., on demand, as discussed further below, continuously, or according to a predetermined profile. When it is desired to generate an intermittent volatilized liquid, the material in liquid form may be supplied intermittently to the heating zone 226 located between terminals 227a, 227b each time that it is desired to generate the precursor vapor or aerosol. Additionally, in intermittent operation the heater could be turned off to prevent liquid in the flow passage from volatilizing. Preferably, the material in liquid form flows from the source 233 of material to the heating zone 226, via a pump 235, pressurized source or other suitable supply arrangement.

One or more valves may be provided in a flow line between the source 233 of material and the heating zone 226 to interrupt flow of liquid. Preferably, the material in liquid form is pumped by a pump 235 in metered amounts (e.g., predetermined volume, mass, flow rate, etc.) to the heating zone 226. The remaining material in the flow line between the source 233 of material and the heating zone 226 provides a barrier to prevent expansion of the volatilized material in the direction of the upstream end 231 of the flow passage 223. The pump can be operated by a stepping motor to achieve precise metering of the liquid material. However, other arrangements can be used to deliver liquid to the flow passage 223, e.g., a syringe pump, which holds a quantity of liquid and delivers precise quantities of liquid or delivers liquid at a constant flow rate; a single shot delivery mechanism, which delivers a precise volume of liquid; a pressurized liquid container arrangement, which delivers liquid to a solenoid valve, which controls delivery of the liquid to the flow passage 223, etc.

FIG. 3 illustrates an embodiment of an instrument 300 for controlled vaporization of liquid material. The instrument includes a flow passage 323 with a downstream first open end 325, heater 310 for heating the flow passage 323 to a temperature sufficient to volatilize liquid material in the flow passage 323, such that the volatilized material expands out of the open end 325 of the flow passage and, if desired, mixes with ambient air to form an aerosol.

Figure 5:
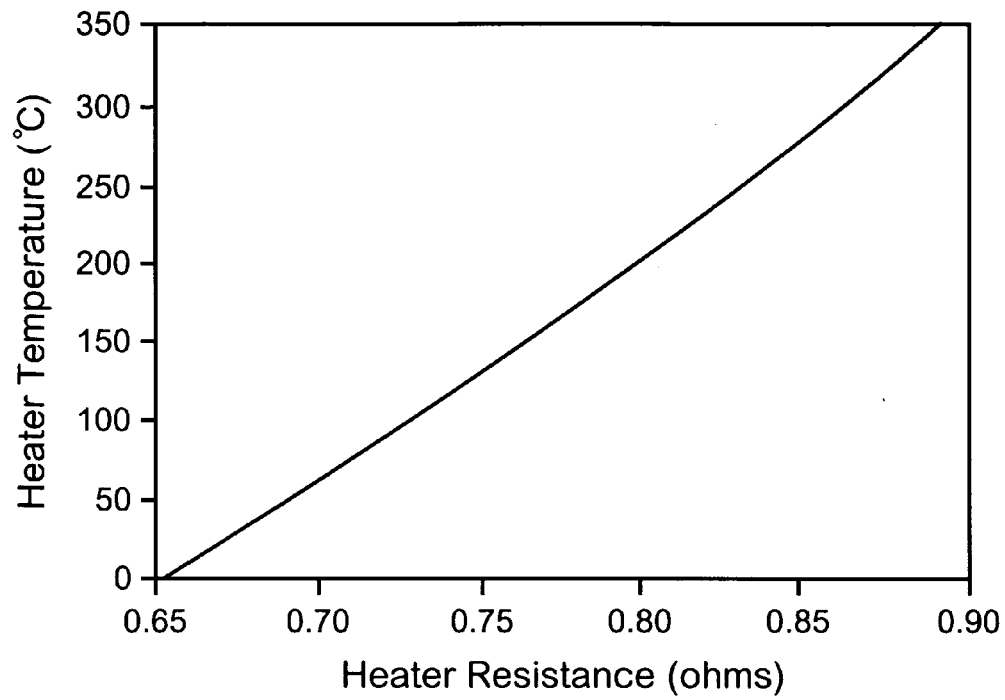
FIG. 5 is a plot of temperature versus resistance of a resistance heater.

The instrument 300 includes a controller 350 for operating the heater 310 and delivery of liquid from liquid source 333 to the flow passage via operation of a valve 342 and pump 335. The controller 350 also directs the storage of parameters associated with generating the volatilized liquid in a memory 351. The controller 350 also operates a switching arrangement or switch 340 for applying power to the heater 310. The memory 351 is provided for recording parameters such as liquid material flow rate and energy transfer, as well as storing operational programs. The maintaining and/or recording of associated parameters with respect to operation of the volatilized liquid generator may be desired when conducting experiments or monitoring quality of the precursor vapor and the aerosol. Also associated with the controller 350 is a display 352 to assist a user in visually monitoring the generator while in operation and also for displaying the user settings and the contents of the memory 351.

The heater 310 can be activated by application of a voltage across an electrically conducting portion thereof or other suitable arrangement. For instance, a heating element can be comprised of a coil of wire or a layer of conductive material along the flow passage 323. The use of a heat exchanger or exposure to combusted gases could also be used to heat the flow passage. Lasers, and electromagnetic waves, as well as chemical and mechanical methods of vaporizing liquid in the passage, are also possible. The resistance heating arrangement heats the liquid material inside the flow passage, in the particular embodiment by converting electrical energy into heat energy as a result of the electrical resistance of the tube or heating element and the voltage and induced current supplied across it. The voltage is applied by a power source 329 across the terminals of the heating element 327*a* and 327*b*. The application of voltage to the heater 310 is regulated, by the controller 350, through manual inputs or an operating program, through a switch 340. In this embodiment, the switch 340 is a field effect transistor which allows rapid switching through cycles less than 10 milliseconds, preferably less than 1 millisecond.

The controller 350 receives input relating to the temperature of the flow passage 323, through a measuring device 341 and input relating to the flow rate of the liquid material into the flow passage 323 from a measuring device 342. Venturi channels, positive displacement pumps and other equipment capable of such measurements can be used as the measuring device 342. The temperature of the liquid in the flow passage 323 is calculated based on the measured or calculated resistance of the heating element. In a preferred embodiment, the heater 310 is a portion of a metal tube, or the heater can be a strip or coil of resistance heating material. The controller 350 regulates the temperature of the flow passage 323 by monitoring the resistance of the heater.

Resistance control can be based on a simple principle that the resistance of the heater 310 increases as its temperature increases. As power is applied, via switch 340, to the heating element 310, its temperature increases because of resistive heating and the actual resistance of the heater also increases. When the power is turned off, the temperature of the heater 310 decreases and correspondingly its resistance decreases. Thus, by monitoring a parameter of the heater (e.g., voltage across the heater using known current to calculate resistance) and controlling application of power, the controller 350 can maintain the heater 310 at a temperature that corresponds to a specified resistance target. The use of one or more resistive elements could also be used to monitor temperature of the heated liquid in cases where a resistance heater is not used to heat the liquid in the flow passage.

The resistance target is selected to correspond to a temperature that is sufficient to induce a heat transfer to the liquid material such that liquid is volatilized and expands out the first open end 325 of the flow passage 323. The controller 350 effects closing of the switch 340, which activates the heating thereby applying for a duration of time, energy to the heater 310 and, after and/or during such duration, determines the real time resistance of the heater, using input from the measuring device 341. In the preferred embodiment, the resistance of the heater is calculated by measuring the voltage across a shunt resistor (not shown) in series with the heater 310 (to thereby determine current flowing to the heater) and measuring the voltage drop across the heater (to thereby determine resistance based on the measured voltage and current flowing through the shunt resistor). To obtain continuous measurement, a small amount of current can be continually passed through the shunt resistor and heater for purposes of making the resistance calculation, and pulses of higher current can be used to effect heating of the heater to the desired temperature.

If desired, the heater resistance can be derived from a measurement of current passing through the heater, or other techniques can be used to obtain the same information. The controller 350 then makes decisions as to whether or not to send an additional duration of energy based on the difference between the desired resistance target for the heater 310 and the actual resistance as determined by the controller 350.

In a developmental model, the duration of power supplied to the heater was set at 1 millisecond. If the monitored resistance of the heater 310 minus an adjustment value is less than the resistance target, the controller 350 is programmed to supply another duration of energy by leaving the switch 340 in the closed ("on") position. The adjustment value takes into account factors such as heat loss of the heater when not activated, the error of the measuring device and a cyclic period of the controller and switching device, among other possibilities. In effect, because the resistance of the heater varies as a function of its temperature, resistance control can be used to achieve temperature control.

The equation for the temperature coefficient of resistivity for type 304 stainless steel is:

$$\rho(\text{ohm-cm}) = 4.474 \times 10^{-5} + 1.0 \times 10^{-7} T - 3.091 \times 10^{-11} T^2 \quad (4)$$

where T is the temperature in degrees Kelvin. A plot of the average temperature of a heater comprising a 28 gauge, 44-mm long capillary tube with a cold resistance (room temperature, 24 C) of 0.669 ohms as a function of its resistance is shown in FIG. 5. The values shown in FIG. 5 represent the average temperature of the heater, i.e., the actual temperature along the length of the heater can vary due to factors such as heat losses from the electrical leads and the vaporization of the fluid, and the temperature of the heater proximate the end 331 and the open end 325 of the flow passage 323 will tend to be lower than in the middle of the heater.

The controller 350 can be programmed to determine the resistance of the heater 310 by processing data representative of the voltage drop across a shunt resistor and voltage drop across the heater. The cumulative energy sent to the heater, the real time resistance of the heater, and the power being sent to the heater are calculated by the following equations:

$$\text{Energy}_{k+1} = (\text{Input 1} * \text{Input 2} * 0.100 * \text{Energy Coef}) + \text{Energy}_k \quad (5)$$

$$\text{Resistance} = (\text{Input 1}/(\text{Input 2}*100)) * \text{Resist Coef.} \quad (6)$$

These equations are based on Ohm's Law. "k+1" and "k" represent the cumulative nature of equation (5). Input 1 is a multifunction measurement and control unit that measures the voltage drop across the heater, and Input 2 is the input terminal that measures the voltage drop across the shunt resistor. While the shunt resistor can have a resistance of 0.010 ohms, exemplary embodiments are not so limited and other resistances are contemplated. For example, the shunt resistor can have a resistance of 0.050 ohms. Such a resistance can provide a better signal-to-noise ratio. The energy in joules can be represented as:

$$\text{Energy} = \text{Power} \times \text{Time} = V_{heater} * I * t. \quad (7)$$

where $V_{heater}$ is the voltage drop across the heater (Input 1), I is the current through the system, and t is the duration time (e.g., 1 millisecond) of power applied to the heater. The current through the system can be calculated from the voltage drop across the shunt resistor and its known resistance as follows:

$$I = V_{shunt}/R_{shunt} \quad (8)$$

$$\text{Energy} = \text{Input 1} * (\text{Input 2}/0.01 \text{ ohm}) * 0.001 \text{ sec} \quad (9)$$
$$= \text{Input 1} * \text{Input 2} * 0.100$$

where $V_{shunt}$ is the voltage drop across the shunt resistor (Input 1) and $R_{shunt}$ is the resistance value of the shunt resistor (0.010 ohm). As discussed above, the resistance value of the shunt resistor can be chosen from a range of resistances such as from 0.010 ohms to 0.050 ohms, for example.

The energy per duration value can be corrected for instrumental variations with a calibration factor, ECF. The duration energy is added to the previous energy value stored in the memory 351 so that the instrument keeps track of the cumulative energy sent to the heater 310. Likewise for the resistance value of the heater:

$$\text{Resistance} = V_{heater}/I \quad (10)$$
$$= (V_{heater}/(V_{shunt}/R_{shunt}))$$
$$= (\text{Input 1}/(\text{Input 2} * 100))$$

The resistance value is then corrected by a calibration factor, RCF.

Figure 6:
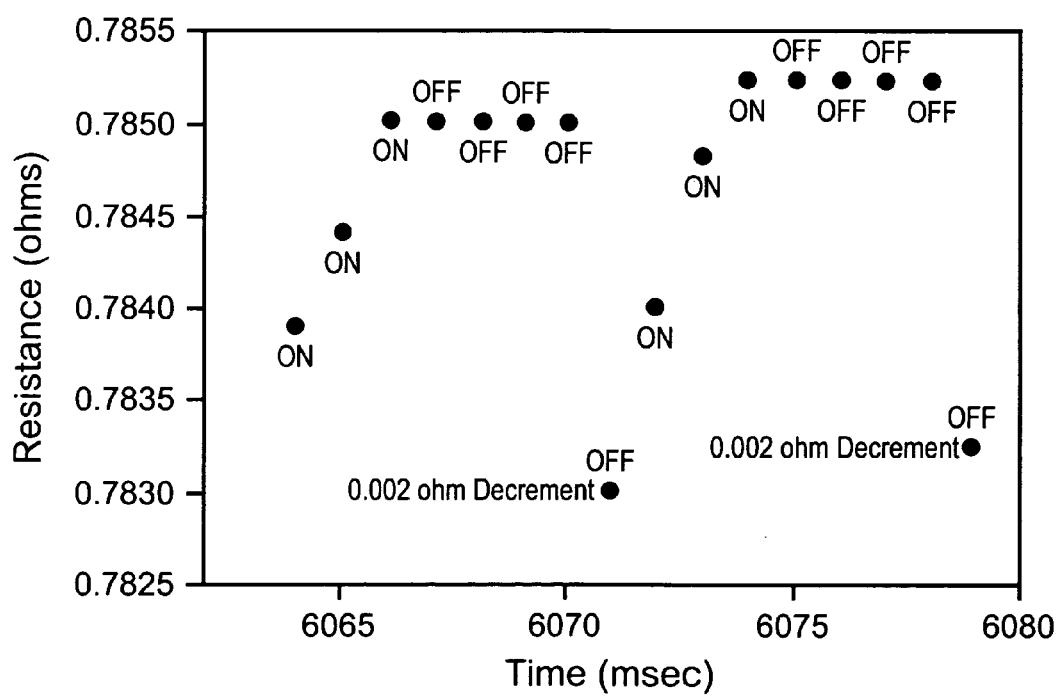
FIG. 6 is a plot of resistance of a resistance heating element versus time, the plotted points indicating when the heating element is supplied power and when the heating element is not supplied power.

Control of resistance by the controller 350 offers several advantages for controlling the heater. First, when the heater 310 is initially started, the controller 350 can send energy continuously to the heater 310 until it reaches its operating resistance target or a lower value to prevent initial overheating the heater after which the heater can be heated gradually to the desired temperature. This provides the fastest start up of the heater. Second, the controller can automatically adjust the energy being sent to the heater to match the requirements for maintaining the resistance target without regard to the delivery rate of the liquid material, at least to the upper limit of the power source 329. As long as the resistance target and corresponding temperature is set within the material limits of the heater 310, the heater cannot be overheated due to a failure in the fluid supply system. An example of a heating cycle is depicted in FIG. 6, which illustrates the timing cycle for the resistance control algorithm, the resistance target in this example being 0.785 ohms. This also protects against over heating due to the power supply voltage being set too high. In addition, this system was found to respond much faster than an actual temperature control system based on thermocouple measurements.

If the measured resistance of the heater minus the predetermined adjustment value is greater than the target resistance at the end of a pulse duration, the controller 350 turns the switch 340 off, thereby withholding energy from the heater 310. After another predetermined duration, the controller turns the switch 340 on and repeats the process. For example, the second predetermined duration can be set at 8 msec (e.g., 2 milliseconds on and 6 milliseconds off or 4 milliseconds on and 4 milliseconds off, etc.) from the previous occasion when the switch 340 was turned on.

In alternative embodiments, various protection features are programmed with the software of the controller 350. An Over Resistance Protection (ORP) feature allows the vapor generator controller software to shut power off to the heater 310 and stop fluid delivery, within 1 millisecond, of the measured resistance exceeding a user-specified threshold. An Over Pressure Protection (OPP) feature, when coupled with a pressure sensor, allows the vapor generator controller software to shut power off to the heater 310 and stop fluid delivery, within 1 millisecond, of the measured pressure of the liquid material exceeding, or optionally falling below, a user-specified threshold. An Under Energy Protection (UEP) feature allows the vapor generator controller software to shut power off to the heater 310 and stop fluid delivery if the measured delivered energy, over a user-specified time interval, falls below a user-specified threshold. Each of the user-specified thresholds can be entered by means of a user interface or can, optionally, be implemented through programmed default values, thereby protecting the equipment of the vapor generator.

Figure 4:
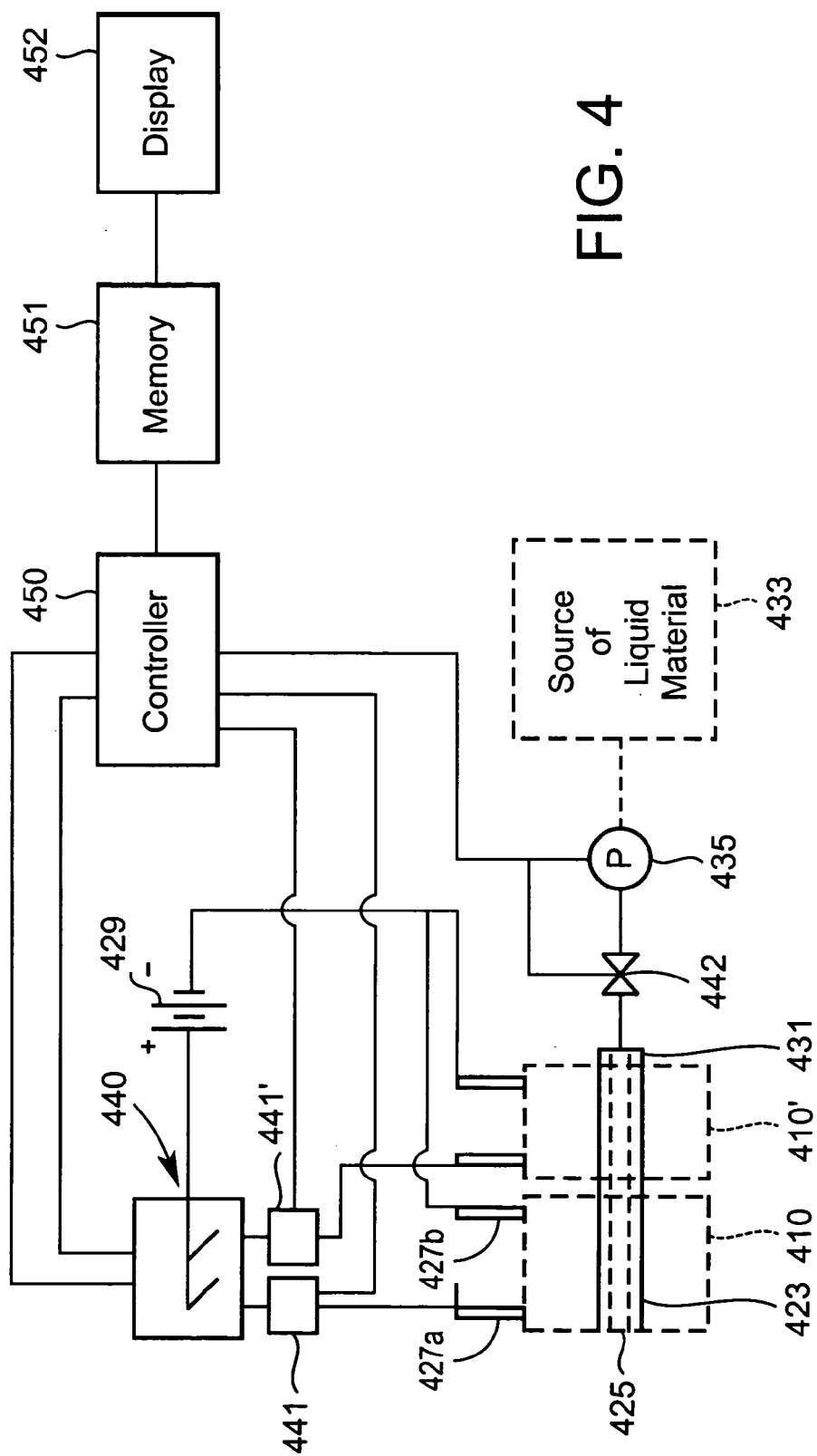
FIG. 4 shows an embodiment of an instrument wherein multiple heating zones heat the liquid.
Figure 7:
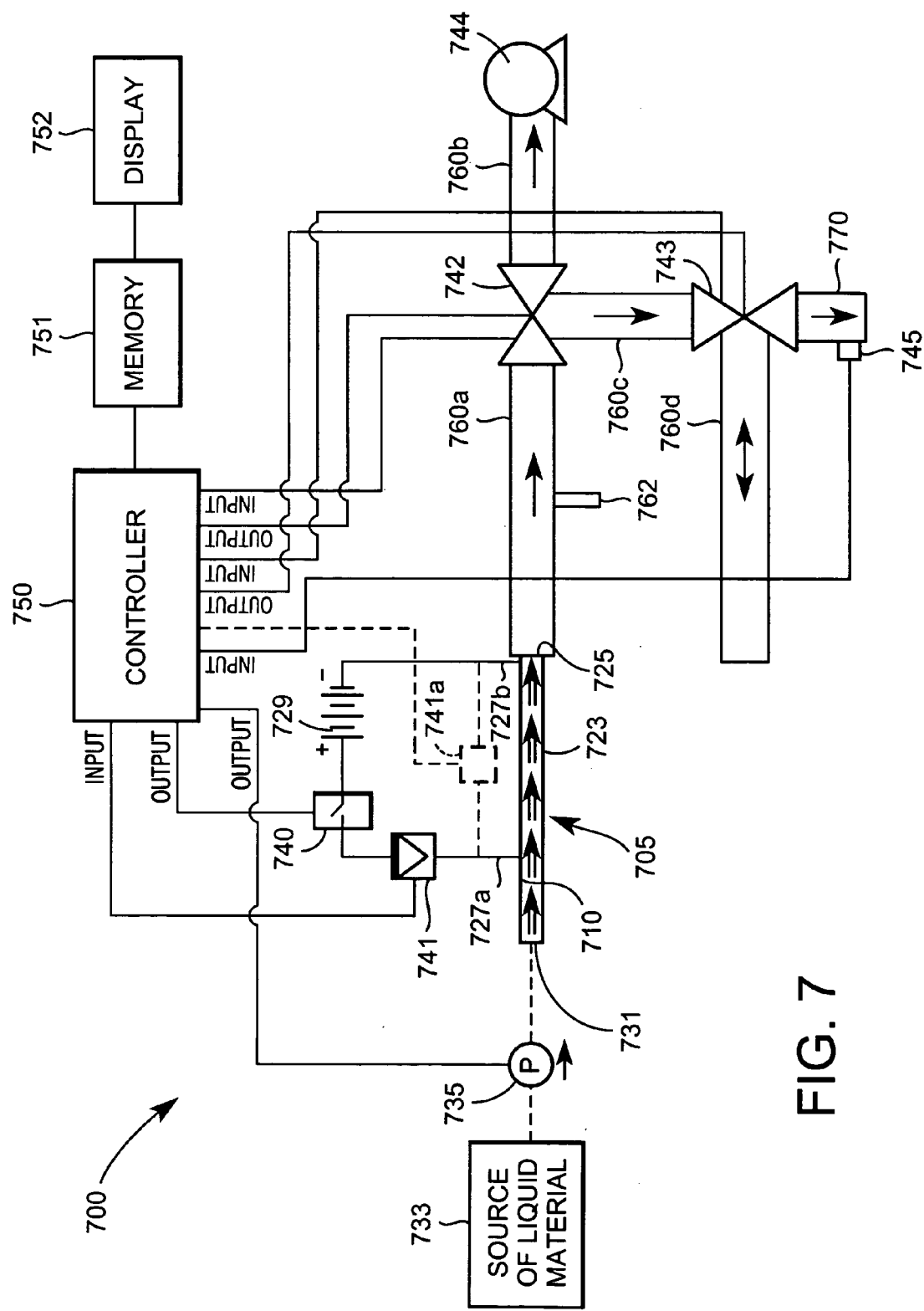
FIG. 7 shows another embodiment of an instrument wherein a controller operates a fluid supply and heater arrangement.

Yet a further embodiment provides for a profiler module to create one or more resistance-power profiles for controlling the operation of the vapor generator. While exemplary embodiments provide for automatic delivery of power to the heaters such that a target resistance is achieved and maintained, all embodiments are not so configured. An alternative embodiment provides for a software program directed toward creating one or more profiles for controlling the operation of a vapor generator, such as shown in FIGS. 3, 4, and 7. The profiling embodiment can create a plurality of profiles that permits simplified and/or automatic operation of the vapor generator across multiple power, resistance, flow, etc. settings with minimal, if any, user input. In such a manner, the vapor generator can automatically compensate for variances found within the components of the vapor generator, such as heaters that require more or less power to vaporize a particular fluid.

Figure 9:
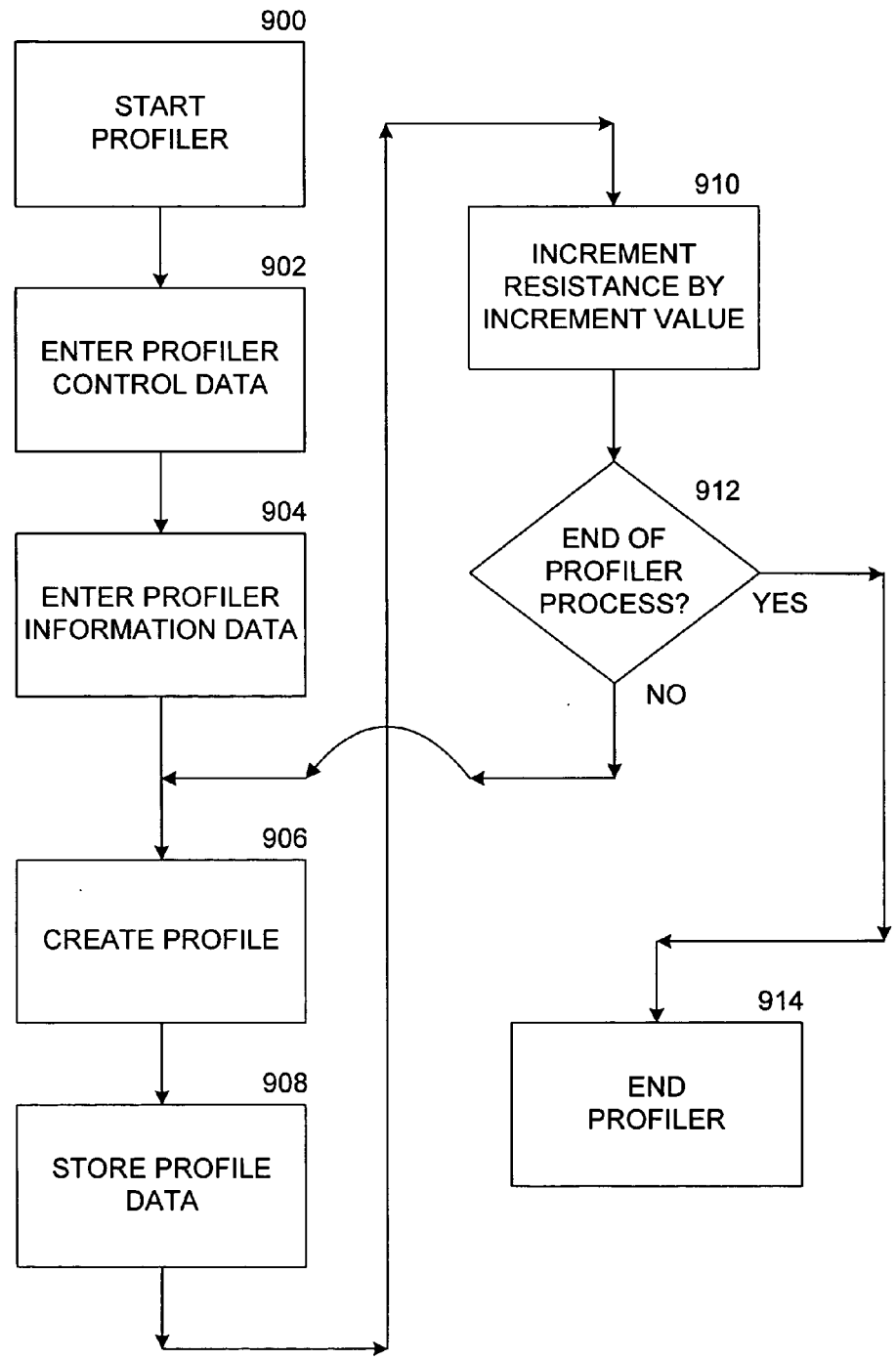
FIG. 9 shows a block diagram of a method for creating one or more profiles for controlling the operation of a vapor generator.

Referring now to FIG. 9, there is shown the steps of a computer-based method for creating one or more profiles for controlling the operation of a vapor generator. The resulting resistance-power profiles can subsequently be selected by a user to automatically control the operation of the controller and the generator, based on resistance, delivered power, energy, and/or other control parameters.

At step 900, the profiler is started by either manual command of a user through a user interface to the controller, or by the user interface automatically detecting a change in the operating parameters. The user then enters profiler control data at step 902. The control data includes a power range for the one or more heaters of the generator. An exemplary range can be from 7 to 11 watts. Alternatively, for those generators comprising multiple heaters, the user is given the option through the user interface of entering different power ranges for each of the plurality of heaters. Further, the user can enter a maximum power value, such as, for example, 9 watts. If the power draw exceeds the maximum power value, an Over Power Protection feature can be triggered, shutting off power to the heaters and stopping fluid delivery. The user also enters the voltage of the power supply for energizing the heaters. The voltage value, for example and not limitation, can be in the range of 4.0 to 5.5 volts. The off time for the heater duty cycle is also set by the user. This value can default to 4 milliseconds if no off time is provided by the user. Similarly, each of the control parameters can be programmed to a default value to simplify the process of creating generator operation profiles.

The heater delay time can also be set by the user. In exemplary embodiments, the heater delay time can default to 0 milliseconds such that the heater and the pump are energized simultaneously. Alternatively, the user can indicate that the heater should start a specified amount of time before (a negative time value) or after (a positive time value) the pump is energized. The user can also set the start resistance for the heater in ohms, such as 1.0 ohms. Each heater is specified as having, or can be calibrated to determine, a cold resistance value. In one embodiment, the start resistance for each heater can be set at 15% over the heater's cold resistance value. Further, a resistance increment value can be entered by the user, such as 0.01 ohms (10 milliohms). The resistance increment value is the incremental value by which the resistance is increased for each iteration of the profiler, as shown in steps 906 through 912.

At step 904, the user can enter the profiler information data. The information data is the information that is relevant to the operation of the vapor generator but does not necessarily control the generator's operation. For example, the operator or user can enter his or her name. In this manner, the subsequent profiles can be identified by the individual entering the control parameter data to the profiler process. The heater code for each heater of the generator can also be entered here. The heater code can be taken from the exterior of each heater. The formulation of the liquid material to be pumped through the heater is also entered here, such as, for example, a 3% solution of CrNa. The pump flow rate, such as, for example, a value between 5 milliliters per second and 7.5 milliliters per second, can also be entered. The information data can subsequently become part of the created control profiles, can be uploaded to data files created during the profiling process, and can be displayed through a user interface.

In an alternative embodiment, the pump flow rate can be entered as control data instead of information data, wherein the controller is programmed to control the operation of the pump based on the user-entered pump flow rate and the subsequent profile instead of a manually-set or pump-fixed pump flow rate. Embodiments further envision the liquid formulation being a control parameter, whereby the software can accommodate the requirements of different liquid material formulations, such as providing for a higher resistance to the heaters or energizing the pump prior to energizing the heater(s).

At step 906, the software of the profile module automatically triggers, for a limited period, operation of the vapor generator, using the entered and default control data. Using the start resistance value as a target, the profile module operates the generator, including providing power to the heater(s) and the fluid delivery, for a fixed time, such as, for example, 2 seconds, and determines the power required to operate the heater(s) to the target resistance value without exceeding the target resistance value, with the start resistance value being the target value during the first iteration of the profiler. At the end of the fixed run time, the targeted resistance value and the determined power level are stored as profile data in step 908. For example, the profile data can be recorded in a log file, which can include all or part of the entered control and information data associated with each profile, such as power supply voltages, liquid formulation, and heater codes.

The resistance value is incremented by the resistance increment value at step 910 to create a new target resistance value. At step 912, the profile module checks to determine whether the profiler process is complete. For example, if the incremented resistance value exceeds a user-specified maximum resistance for the heater, the profiler process ends at step 914. Also, if the profiler process has proceeded through n iterations, where n is a user-provided integer greater than 0 or defaults to a value, such as, for example, 3, the profiler process ends. Otherwise, control passes back to step 906 to create an additional profile based on the incremented resistance value and the remaining control data. It is noted that steps 910 and 912 can be reversed without departing from the spirit of exemplary embodiments in that checking for the end of the profiler process can occur before incrementing the resistance for the next iteration of the profile creation method.

In exemplary embodiments, one or more control parameters, in addition to or instead of the heater resistance values, can be incremented or modified, for creating control profiles for subsequent operation of the vapor generator. For example, the flow rate of the liquid material through the heaters can be varied, with a profile being created for each flow rate provided to the profiler. In this manner, multiple profiles can be created and stored for subsequent access by a user. It is noted that all created profiles are not necessarily good or usable profiles. For example, a profile can indicate a power requirement that is above user-desired parameters. In this manner, the profile process can provide profile data useful to an operating environment where the undesirable operation of a vapor generator is to be avoided, such as where a heater or other component of the vapor generator can be prematurely damaged or rendered unusable.

At the conclusion of the profiler process, one or more profiles have been created and stored in memory or in storage for subsequent access for controlling operation of the vapor generator, including directing the operation of the programmed controller. In this manner, the profiler process provides for the programmed controller to teach itself to initiate and operate the vapor generator according to desirable and/or user-specified parameters. In one embodiment, the profile data can be stored as an .xml file for subsequent access by the controller to automatically control operation of the generator.

Figure 10:
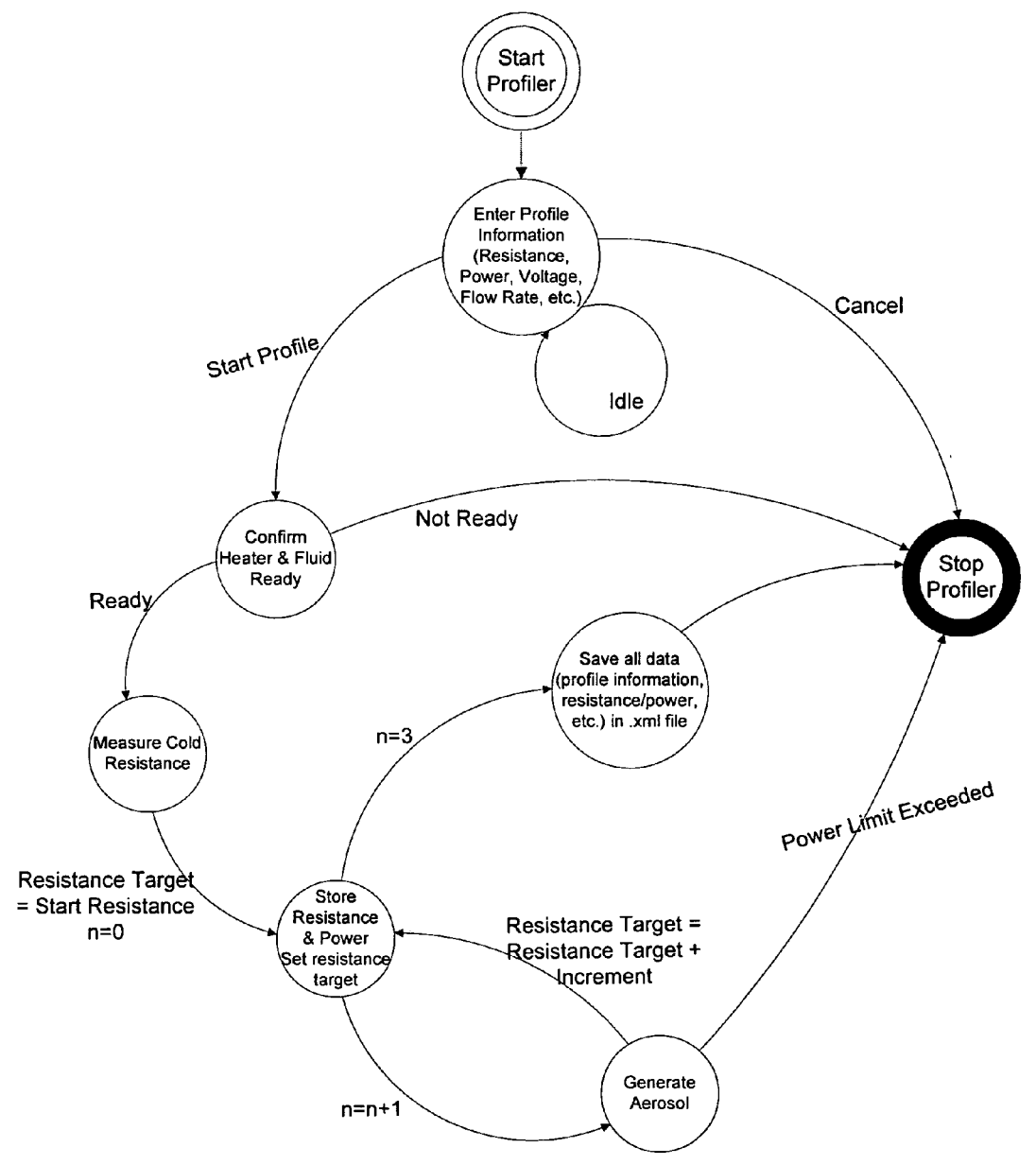

An alternate view of the profiler process is shown in FIG. 10, where more of the branching and conditions of the profiler process are shown. It is noted that the flow shown in FIG. 10 is for 3 iterations of the profiler process, thereby creating 3 profiles for the subsequent automated operation of the vapor generator.

Figure 11:
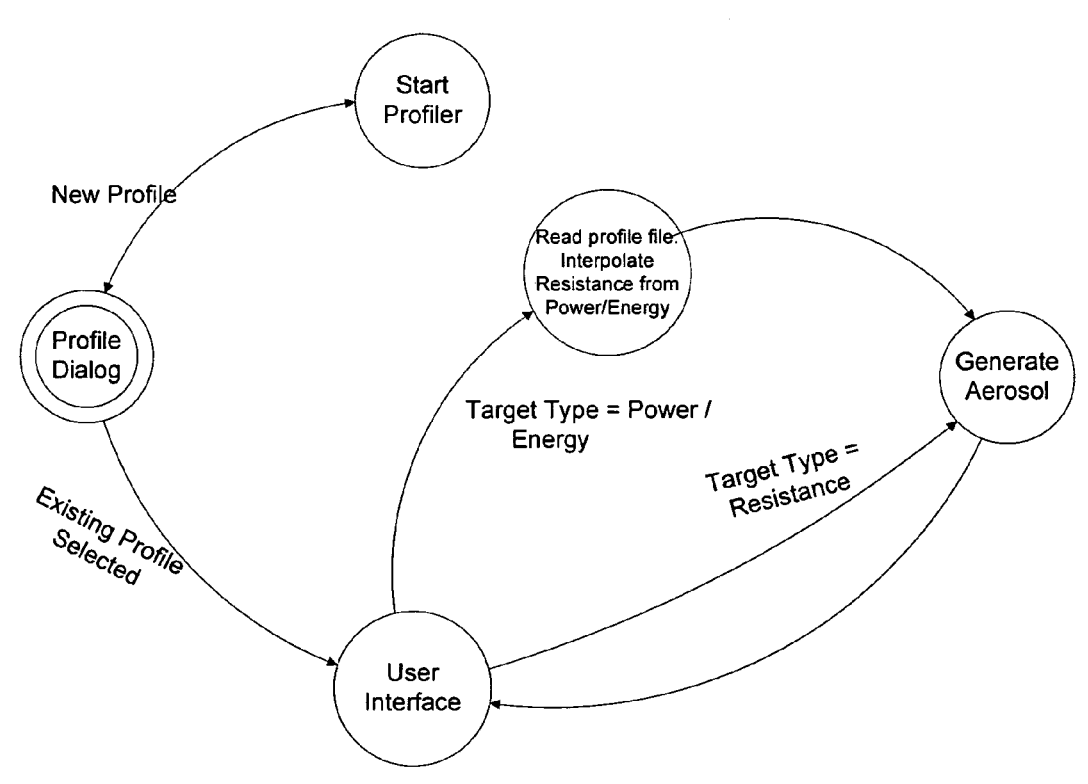

When the user is ready to operate the vapor generator, the user, through a user interface as shown in FIG. 11, can select a profile of choice, such as a profile with a desired liquid formulation, flow rate, power setting, and/or resistance value. In this manner, the user has the option of selecting a profile that targets one or more desired parameters, such as fluid material, resistance, delivered power, and/or energy level. The programmed controller inputs the data of the selected profile and utilizes the data to automatically control operation of the vapor generator within predetermined parameters. Through creation and use of the various profiles, the vapor generator is available for immediate use without need for prior calibration; and the operation of the vapor generator can be quickly changed to adjust to changing conditions and/or modified target performance.

FIG. 4 shows details of an additional embodiment of an instrument for generating a volatilized liquid in which a plurality of separate heaters are used to heat the flow passage and the liquid material passing therethrough such that the material is volatilized and expands out the open end of the channel. As in the previous embodiments, a flow passage 423 with a first open end 425 has a liquid material supplied to it through an end 431, a valve 442 controls the introduction of the liquid, which is supplied from a source of liquid material 433 by a pump 435. In this particular embodiment, two separate heaters 410 and 410' are used to heat the flow passage and the liquid. The heating can be accomplished through resistant heating. However, as discussed earlier, the heating is not limited to this method.

Power is supplied to each of the heaters through terminals 427a and 427b for heater 410 and terminals 427a' and 427b' for heater 410'. The application of power to the heaters is controlled by controller 450 with an associated memory 451 and a display 452. The controller 450 controls the application of power through a switching circuit 440 or other suitable arrangement for power control. The switching circuit is capable of applying power independently to each of the heaters. The power is supplied by voltage source 429. The controller controls the application of power to the heaters separately using information from measuring devices 441 and 441' as well as input from the valve 442. The controller is capable of being programmed to function autonomously or in response to a user interaction.

Measuring devices 441 and 441' in this particular embodiment measure the current through a shunt resistor and are combined with voltage drop across the respective heaters to determine the resistance of the heaters, which facilitates control by the controller 450 as described previously. As discussed above, the temperature across the flow passage 423 can vary from the end 431 where liquid material is supplied to the open end 425 where the material exits as a vapor. As such, the use of a plurality of separate heaters to control the temperature of the flow passage and the liquid therein is advantageous because of different heat transfer characteristics across portions of the flow passage. To further regulate heat transfer of the flow passage to the liquid, additional heaters can be added and controlled as desired.

For those vapor generators comprising multiple heaters, a standby feature permits automatic switching of heaters when one or more heaters is determined to be underperforming or malfunctioning. For example, when the standby feature is enabled by the user or by default, and the controller determines that a heater is under performing or malfunctioning (either via ORP, OPP, UEP, or direct user determination), the vapor generator controller software automatically switches, as fast as within 1 millisecond, to any other heater designated as standby in the vapor generator software or parameters.

Similarly to FIG. 3, heat transfer to the liquid material from the heaters can actually be accomplished using a single heater with different heating zones. For example, a single heater having different zones can apply more heat at a desired location along the flow passage, e.g., more heat at one end of the flow passage 423 and lesser heat in the middle as desired. Although dynamic control of the different heating zones would be more difficult, a more desirable heat profile could be obtained using only the single heater. Multiple zone heating could be achieved with a heater having multiple coils with a high resistance value placed on the end of the flow passage, whereas in the middle the resistance value of the heating element could be reduced and therefore reduce heat transfer to that section. In addition, a pre-heater could be used to heat the material prior to entry to the flow passage to a temperature just below the point at which the liquid material would volatilize.

Embodiments of the instrument can be designed to deliver a desired, specific quantity of vaporized liquids by controlled output of the heater arrangement. For example, the heater arrangement can be connected to multiple fluid flow paths, such as conduits or tubing. The aerosolized output may be conducted through different paths by manipulation of valves. Valve control permits the aerosolized output to be directed to different exits, for a predetermined time interval. For example, the vapor/aerosol can be directed through a first flow path when the heater is in a non-conforming condition (e.g., non-steady state condition), and a valve arrangement can direct the vapor/aerosol through a second flow path when the heater is in a conforming condition (e.g., steady state condition). Embodiments of the instrument can be used for clinical studies in which a constant, repeatable dose is desired to be administered to human volunteers.

FIG. 7 illustrates an embodiment of an instrument 700 for controlled vaporization of liquid material, and selective delivery of aerosol. The instrument 700 includes a member 705 defining a flow passage or channel 723 capable of conducting a fluid or vapor to a first open end 725, and a power source 729 for applying a voltage to the member 705 such that a current in the member heats the flow passage to a temperature sufficient to volatilize a liquid material in the flow passage 723, the volatilized material expands out of the open end 725 of the flow passage 723 and, if desired, mixes with the ambient air to form an aerosol. Liquid can be supplied from a source 733 of liquid material by a pump 735 or other suitable mechanism.

The flow passage 723 in this embodiment is preferably 304 stainless steel. However, any electrically conducting material capable of being resistively heated, retaining the necessary structural integrity at the operating temperature experienced by the flow passage 723, and sufficiently non-reactive with the liquid could be used. Such materials include, but are not limited to, copper, aluminum, metal composites, or other metals or alloys. The flow passage 723 has an outlet 725 that allows the heated material to escape and an inlet 731 that allows the liquid material to be supplied.

The instrument 700 also includes valves 742 and 743. Valves 742 and 743 are actuated by the controller 750. The valve 742 is in fluid communication with the heater via a flow passage 760a and directs vaporized material or aerosol from the heater 710 to the valve 742. Aerosol can be formed, if desired, by mixing vaporized material generated by the heater 710 with air present in and/or supplied to the flow passage 760a. For example, an optional air inlet 762 may be arranged to introduce air into the flow passage 760a, or air may be entrained around the heater 710 and drawn into the flow passage 760a. The valve 742 is in fluid communication with an exhaust vacuum pump 744 via a flow passage 760b, and is in fluid communication with a valve 743 via a flow passage 760c. Valve 743 is in fluid communication with a flow passage 760d. The pump 744 includes a filter, preferably a high efficiency particulate air (HEPA) filter, to remove material from the aerosol or vapor before the air is exhausted to the atmosphere. Flow passages 760a, 760b, 760c and 760d are preferably made of medical grade respiratory tubing. Valve 743 is in fluid communication with a mouthpiece 770, through which a user can inhale aerosol. However, the mouthpiece 770 can be omitted or replaced with any suitable equipment, such as analytical equipment, collection devices, etc.

In the case of an inhaler, the instrument preferably includes a pressure sensor 745 electrically connected to the controller 750 and in fluid communication with the mouthpiece 770. The pressure sensor 745 is activated by a user inhaling on the mouthpiece 770. The inhalation causes a pressure drop in the mouthpiece 770, which is sensed by the pressure sensor 745. The pressure sensor 745 can be extremely sensitive. For example, the pressure sensor 745 can be triggered at a selected pressure drop and/or threshold value of air flow, for example, as low as about 3 liters/min, which is about 1/10 of the typical human inhalation rate. Accordingly, the pressure sensor 745 can be triggered by a user without wasting appreciable lung volume.

Valves 742 and 743 preferably operate in the following manner. When valve 742 is in its default position, the aerosol can flow along a first flow path. Namely, flow passage 760a carries aerosol from the heater 710 to the valve 742, and the flow passage 760b carries aerosol from valve 742 to the pump 744. The aerosol is filtered by the filter provided in the pump 744 and exhausted to the environment. When valve 742 is in its default position, the flow passage 760c is empty (i.e., there is no aerosol moving through it). Accordingly, no aerosol flow is permitted to the mouthpiece 770.

When valve 742 is in its default position, valve 743 is also in its default position. When valve 743 is in its default position, flow passage 760d directs ambient air through valve 743 to mouthpiece 770.

In preferred embodiments, the aerosol generated by the heater 710 is exhausted to the pump 744, and aerosol flow is not supplied to the mouthpiece 770, until the heater 710 reaches a conforming condition. For example, a monitored condition of the heater 710 can be resistance, and the conforming condition can be when the measured resistance reaches a steady state condition, e.g., nearly constant at the resistance target. In the steady state condition, the aerosol that is generated is thus optimal for human inhalation. The conforming condition may alternatively be, for example, a selected temperature range of the flow passage 723. Once a desired condition of the heater 710 is achieved, aerosol can be delivered to the mouthpiece 770 via a second flow path.

The instrument 700 can operate such that the valves 742 and 743 remain in their non-default positions for a selected period of time, during which aerosol is delivered to the mouthpiece. The selected period of time is not limited and can be, for example, 2/3 second, 1 second or 2 second. Once the selected period has expired, under control of the controller 750, the valves 742 and 743 are moved to their default positions, and aerosol delivery to the flow passage 760c and mouthpiece 770 is terminated.

Figure 8:
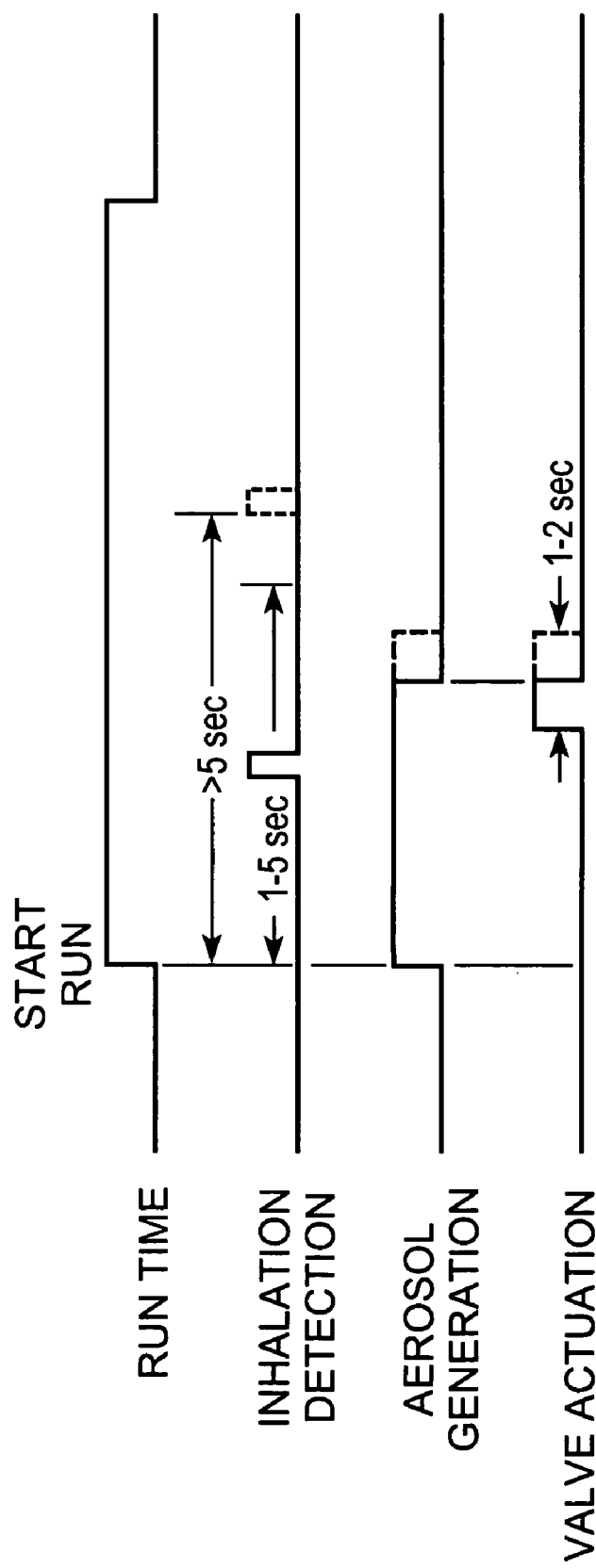
FIG. 8 illustrates an exemplary timing diagram for operation of the instrument shown in FIG. 7.

The instrument 700 can also operate such that vapor generation is terminated unless a user inhales on the mouthpiece 770 within a predetermined period of time after the user has been instructed to inhale. For example, the instrument may include a displayed message or light, which informs the user that the instrument is ready to deliver a dose of medicated aerosol. Alternatively, the pressure sensor 745 can indicate that the user is attempting to receive a dose of aerosol, but if the user stops inhaling for a predetermined period of time, the instrument will shut off the heater 710 and maintain the values in the default condition. Thus, if within the predetermined time period the controller 750 stops receiving signals from the pressure sensor 745 that indicate a user is inhaling on the mouthpiece 770, the controller 750 terminates generation of the volatilized material by the heater 710. For example, the time period can be 5 seconds. If, within the selected time period, the controller 750 receives a signal from the pressure sensor 745 indicating that it has been triggered by a user inhaling on the mouthpiece 770, the controller 750 moves the valves 742 and 743 to their non-default positions so that volatilized material or aerosol flows through the flow passage 760c and to the mouthpiece. FIG. 8 illustrates an exemplary embodiment of a timing diagram for the operation of the instrument 700 for a selected time period of 5 seconds, indicating instrument run time, inhalation detection (by the pressure sensor 745), aerosol generation and valve actuation cycles.

In other embodiments of the instrument 700, the mouthpiece 770, pressure sensor 745 and flow passage 760d can be omitted. The valve 743 can optionally be included, if desired. An optional flow passage (not shown) can be provided in place of the mouthpiece. In such embodiments, operation of valve 742 by the controller 750 can direct the volatilized material or aerosol via the flow passage 760c to a detector for analysis. The volatilized material or aerosol can alternatively be used for other purposes, for example, applying coatings, making powders, chemical interactions with other substances, etc.

The controller 750 is operable to control operation of the heater 710 and delivery of liquid from the liquid source 733 to the flow channel 723 via operation of the pump 735. As explained above, the controller 750 receives signals from the pressure sensor 745, and operates valves 742 and 743 and pump 744 to control the flow of aerosol from the heater 710 to the mouthpiece 770. The controller 750 directs the storage of parameters associated with generating the volatilized liquid in a memory 751. The memory 751 can record such parameters with respect to operation of the volatilized liquid generator, which may be desired when conducting experiments, or monitoring quality of the precursor vapor and the aerosol. The controller 750 also operates a switching circuit 740 for applying power to the heater 710. Also associated with the controller 750 is a display 752 to assist a user in visually monitoring the generator while in operation, and also for displaying user settings and the contents of the memory 751.

The vapor generator software includes an event logger. Whenever a targeted event, such as a button pressed, a value changed, a protection value exceeded, occurs in the vapor generator application, a description and time stamp of the event is saved in an event log file. The event log file is unique to that instance of the vapor generator application and aids in the debugging of reported issues. The display module of the controller software includes a steady state resistance and power measurement. This portion of the display module displays the average resistance during steady state (i.e., for example, the last 100 ms or the last second), and the power delivered in the last second.

In an alternative embodiment, a non-constant resistance target feature is provided to the control software. This feature allows the user to specify different target resistances before, during, and/or after aerosol generation. This plurality of non-constant resistance targets can be entered either in the vapor generator software by the user, or read from a data file. There is no inherent limit to the number of resistance targets that can be specified for an aerosol generation run. In this manner, the controller automatically adjusts the operation of the generator during an aerosol generation run, such as by applying or reducing power to the heater(s), to meet the specified resistance targets for each step of the run.

The power supply for applying a voltage in this embodiment includes the power source 729 and two terminals 727*a* and 727*b*. The power source 729 can be a direct current (DC) battery or a direct current power supply. The application of voltage to the heater 710 is regulated, by the controller 750, through manual inputs or operating program, through a switch 740. In this embodiment, the switch 740 is a field effect transistor, which allows rapid switching through cycles less than 10 milliseconds, preferably less than 1 millisecond.

The controller 750 receives input relating to the temperature of the flow passage 723, through a measuring device 741. The temperature of the liquid in the flow passage 723 is calculated based on the measured or calculated resistance of the heating element. In a preferred embodiment, the heater 710 is a metal tube. The controller 750 regulates the temperature of the flow passage 723 by monitoring the resistance of the heater.

As described above, resistance control can be based on the principle that the resistance of the heater 710 increases as its temperature increases. As power is applied, via switch 740, to the heater 710, its temperature increases because of resistive heating, and the actual resistance of the heater 710 also increases. When the power is turned off, the temperature of the heater 710 decreases and correspondingly its resistance decreases. Thus, by monitoring a parameter of the heater (e.g., voltage across the heater using known current to calculate resistance) and controlling application of power, the controller 750 can maintain the heater 710 at a temperature that corresponds to a specified resistance target. The use of one or more resistive elements could also be used to monitor temperature of the heated liquid in embodiments where a resistance heater is not used to heat the liquid in the flow passage.

The resistance target is selected to correspond to a temperature that is sufficient to induce a heat transfer to the liquid material such that liquid is volatilized and expands through outlet 725. The controller 750 effects closing of the switch 740, which activates heating, thereby applying for a duration of time, energy to the heater 710 and after and/or during such duration, determines the real time resistance of the heater using input from the measuring device 741. In a preferred embodiment, the resistance of the heater is calculated by measuring the voltage across a shunt resistor (not shown) in series with the heater 710 (to thereby determine current flowing to the heater), and measuring the voltage drop across the heater (to thereby determine resistance based on the measured voltage and current flowing through the shunt resistor).

To obtain continuous measurement of resistance and energy, a small amount of current can be continually passed through the shunt resistor and heater to make the resistance calculation, and pulses of higher current can be used to effect heating of the heater to the desired temperature and/or a resistance target. In an exemplary embodiment, a profile can specify the optimum power level for running the heater(s) of the generator. Once the desired temperature and/or resistance target is achieved, power can be decreased to a minimal level sufficient to continuously measure resistance and energy without heating the heater.

If desired, the heater resistance can be derived from a measurement of current passing through the heater, or other techniques can be used to obtain the same information. The controller 750 then makes decisions as to whether or not to send an additional duration of energy based on the difference between a desired resistance target for the heater 710 and the actual resistance as determined by the controller 750.

In a developmental model, the duration of power supplied to the heater was set at 1 millisecond. If the monitored resistance of the heater 710 minus an adjustment value is less than the resistance target, the controller 750 is programmed to supply another duration of energy by leaving the switch 740 in the closed ("on") position. The adjustment value takes into account factors, such as heat loss of the heater when not activated, the error of the measuring device, and cyclic period of the controller and switching device, among other possibilities. In effect, because the resistance of the heater 710 varies as a function of its temperature, resistance control can be used to achieve temperature control.

The controller 750 can be programmed to determine the resistance of the heater 710 by processing data representative of the voltage drop across a shunt resistor and voltage drop across the heater. The power being sent to the heater, the cumulative energy sent, and the real time resistance of the heater are calculated by equations (5) and (6) described above. The shunt resistor can have a resistance of 0.010 ohms. Thus, energy in joules is given by equation (7) described above.

The current through the system can be calculated from the voltage drop across the shunt resistor and its known resistance by equation (8) described above.

The energy per duration value can be corrected for instrumental variations with a calibration factor, ECF. The duration energy is added to the previous energy value stored in the memory 751 so that the instrument keeps track of the cumulative energy sent to the heater 710. Likewise, for the resistance value of the heater, equation (10) described above is used. The resistance value is then corrected by a calibration factor, RCF.

Control of resistance by the controller 750 offers several advantages for controlling the heater. First, when the heater 710 is initially started, the controller 750 can send energy continuously to the heater 710 until it reaches its operating resistance target or a lower value to prevent initial overheating of the heater after which the heater can be heated gradually to the desired temperature. This provides the fastest start up of the heater.

Second, the controller 750 can automatically adjust the energy being sent to the heater to match the requirements for maintaining the resistance target without regard to the delivery rate of the liquid material, at least to the upper limit of the power source 729. As long as the resistance target and corresponding temperature is set within the material limits of the heater 710, the heater 710 can be protected from overheating due to a failure in the fluid supply system. An example of a heating cycle is depicted in FIG. 6 described above. This also protects against overheating due to the power supply voltage being set too high. In addition, this system was found to respond much faster than an actual temperature control system based on thermocouple measurements.

If the measured resistance of the heater 710 minus the predetermined adjustment value is greater than the target resistance at the end of a pulse duration, the controller 750 turns the switch 740 off, thereby withholding energy from the heater 710. After another predetermined duration, the controller turns the switch 740 on and repeats the process. For example, the second predetermined duration can be set at 8 milliseconds (e.g., 2 milliseconds on and 6 milliseconds off or 4 milliseconds on and 4 milliseconds off, etc.) from the previous occasion when the switch 740 was turned on.

If desired, the instrument can be provided with multiple vapor generators. For example, two or more flow passages with heaters as described above could be arranged to deliver vaporized liquid to a conduit through which air or other medium is passed. Analytical devices could be located along and/or downstream of the conduit to measure various characteristics of the vaporized liquid, e.g., devices to measure aerosol size and/or particle size distribution, determine effects of chemical interactions of the vaporized liquid, etc. The vapor generators can be arranged to deliver the vaporized liquid as intersecting or non-intersecting gas streams. For example, the flow passages can be arranged to direct the vaporized fluid into the conduit as adjacent parallel gas streams, radially directed, circumferentially spaced apart gas streams or radially directed, axially spaced apart gas streams, etc. The parallel generator arrangement facilitates forming a combination aerosol or precursor vapor formed by mixing together two or more separately generated volatilized liquids. The parallel volatilized liquid generator arrangement is particularly useful where it is desired to form an aerosol comprising two or more materials, which do not mix well in liquid form.

The instrument can be used to study various aspects of aerosol generation, which vary as functions of parameters of the vapor generator and the liquid material supplied to the vapor generator. For example, for aerosols intended for human inhalation, an aerosol can be produced with a mass median particle diameter of particles of the aerosol less than 2 microns, preferably between 0.2 and 2 microns, and more preferably between 0.5 and 1 micron.

It has been observed that liquid materials, such as propylene glycol and glycerol, can be formed into aerosols having mass median particle diameters and temperatures in desirable ranges. While not wishing to be bound by theory, it is believed that the extremely small mass median particle diameters of the aerosol are achieved, at least in part, as a result of the rapid cooling and condensation of the volatilized material that exits the heated flow passage. Manipulation of parameters of the volatilized liquid generator, such as the internal diameter of the flow passage, heat transfer characteristics of the material defining the flow passage, heating capacity of the heater, and/or the rate at which material in liquid form is supplied to the flow passage, can be performed to affect aerosol temperature and mass median particle diameter. The instrument can be used to investigate aerosol formation using propylene glycol and glycerol as liquid carriers for drugs such as budesonide. The instrument can also be used to investigate aerosol formation and/or vaporized fluid properties of liquid materials, such as jet fuel, pesticides, herbicides, paint and other types of materials.

It will be appreciated that the instrument may be fairly large, such as a table-top mounted item, but the principles of the instrument may be implemented in other forms, such as a miniaturized device. The ability of the generator to be miniaturized is, in large part, due to the highly efficient heat transfer between the heater and the flow passage, which facilitates battery operation of the volatilized liquid generator with low power requirements.

The instrument can be implemented as a laboratory unit designed to include programmable operation of a vapor generator, wherein liquid is vaporized by a heater arrangement. The instrument can be modular in construction so that the various components can be exchanged. Aerosol mass median particle diameter can be measured using a cascade impactor in accordance with the methods specified in the Recommendations of the U.S.P. Advisory Panel on Aerosols on the General Chapters on Aerosols (601) and Uniformity of Dosage Units (905), *Pharmacopeial Forum.*, Vol. 20, No. 3, pp. 7477 et. seq. (May–June 1994), and mass can be measured gravimetrically as collected from the impactor.

The basic resistance control program used by the instrument can be adapted for various applications. For example, the liquid can be supplied by a pump and the apparatus can be programmed to generate an aerosol for very long run times. For example, in toxicological studies it may be desired to generate an aerosol for several hours. In such case, it may be desirable to run four heaters simultaneously for an extended period of time, such as 4 hours. In contrast, if the instrument is used to mimic the operation of hand-held inhaler, the run times would be more on the order of 2 to 4 seconds. During extended runs, the operator of the instrument can be kept informed of the operation of the instrument by outputting data to be monitored periodically, such as every 10 seconds.

The optimal resistance target for a heater can be determined experimentally using a standard operating procedure. As the resistance target entered in the instrument control program is lowered from its optimal value, the aerosol quality soon decreases. In particular, more liquid will be ejected from the heater as large droplets and excess fluid will drip from the end of the heater. As the resistance target is increased over its optimal value, aerosol quality will also degrade eventually. For instance, the generator will use more energy needed to produce the aerosol and, at higher resistance target values, significant thermal degradation of the aerosol fluid may occur. In an extreme limit, the heater may begin to glow red and could become damaged.

The voltage chosen to drive the heater determines the amount of energy that will be sent to the heater in each pulse. For 1 millisecond pulses, the energy per pulse in joules is given by the equation: energy=$V^2 t/R$, where V is the voltage across the heater, R is the heater resistance, and t is 1 millisecond. The voltage across the heater is directly related to the voltage of the power supply, but is slightly lower because of losses in the wiring. In general, the lowest voltage that can be used with a preferred embodiment of the instrument is 4 volts. This lower limit is set by the minimum voltage required to operate the field effect transistor (FET).

The instrument is preferably wired such that the power supply providing the power to the heater also provides the switching voltage for the FET. The resistance of the heater at steady state can be assumed to be nearly constant at the resistance target. Thus, changing the voltage can make a large difference in the energy sent in each pulse. The effects of voltage appear mainly in the steady state operation of the heater. If the voltage is too low, the heater may have trouble reaching the resistance target and the aerosol quality can be degraded. If the setting for the voltage is too high in the case where the algorithm uses an 8 millisecond cycle to control the heater, if too much energy is sent in a single pulse the heater may exceed the resistance target by more than 0.002 ohms. In such case, it may take several cycles for the heater to come back on, but by this time the heater may have cooled substantially because of the fluid flow passing through it. Accordingly, the voltage and/or other control parameters can be optimized for a particular flow rate and particular liquid material.

The power required by the heater to produce an aerosol is directly proportional to the fluid flow rate passing therethrough. If the flow rate is very low, e.g., less than 0.1 ml/min, the heater may act as if the voltage is too high. On the other hand, if the flow rate is too high, the heater may act as if the voltage is too low. Raising the voltage may be required to compensate for high flow rates. The length of the timing (duty) cycle is preferably set such that the heater will turn back on before it cools significantly. Experiments with a 32 gauge stainless steel tube as the heater at a flow rate of 0.1 ml/min indicate that timing cycles between 4 and 10 milliseconds have little effect on the aerosol. However, the timing cycle can be changed to compensate for behavior of the heater and/or properties of the aerosol. The goal of resistance control is to keep the operating resistance of the heater very close to the resistance target. As an example, the voltage can be set such that the resistance increase for a single pulse of energy is relatively small. For example, the controller can be programmed to monitor the resistance of the heater and ensure that the resistance target is not exceeded by more than 0.002 ohms when the algorithm turns the heater off. Thus, a 0.002 ohm decrement can be used to trigger supply of power to the heater. In principle, the instrument can be designed to effect operation of the heater with an desired change in the resistance target other than the 0.002 ohm decrement described above.

In an alternative embodiment, an n-point calibration scheme is provided for dynamically calibrating the vapor generator, where energy and resistance calibrations are performed independent of each other. In contrast to contemporary methods for manually calibrating a vapor generator or the like, both the resistance and energy calibrations are automated in exemplary embodiments, and are controlled by the vapor generator software itself. The n-point calibration method calculates resistance and energy correction coefficients that correct for instrument variations. For example, the electrical components of the vapor generator, such as shunt resistors, heaters, and connectors, can be the source of resistance and energy measurement errors which require correction for more accurate operation of the vapor generator. As discussed above regarding equations (5)–(10), single point energy and resistance calibration factors, ECF and RCF, respectively, can be utilized to correct for instrumental variations. In this alternative embodiment, a multi-point calibration/error correction method is utilized to dynamically correct for electrical variations in the operation of the vapor generator.

The new calibration routine differs from previous routines discussed above in association with equations (5)–(10) in that the software provides calibration factors of the form of a linear equation, namely:

$$y=mx+b. \quad (11)$$

The "n" in the n-point calibration scheme represents the number of finite precision resistances across which the operation of the vapor generator is initially calibrated. While "n" can be any integer, for purposes of discussion here and not limitation, a value of 3 will be used for "n." As can be appreciated, increasing the value of "n" can improve the accuracy of the algorithm (11) but at some value, the n-point calibration scheme would encounter a point of diminishing returns. A value for "n" that is greater than 1 would produce a plurality of points, as discussed below, thereby more accurately compensating for the non-linear behavior of the components of the vapor generator in the active region, i.e., within the power and resistance operating range of the vapor generator.

In a 3-point calibration method, or polynomial function, three precision resistances are selected. For example, resistances of 100 milliohms, 500 milliohms, and 1.0 ohm can be selected. The vapor generator is operated automatically under control of its software for a fixed period of time under each of the 3 precision resistances, and the resistance measured and recorded by the vapor generator. Each of the three resistances measured by the vapor generator become "x" values in a 2-dimension graph, and each of the values of the precision resistors become the corresponding "y" values, thereby establishing three points in the graph. Concurrent with the resistance measurements, energy is measured and recorded for each of the precision resistances by the vapor generator and a separate instrument. The linear algorithm (11) is thereby determined, with "m" being the slope of the line through the three points and "b" being the intercept of the line along the y-axis. The slope of the each of the lines becomes the $R_{C1}$ and $E_{C1}$ correction coefficients used in the equations below, and the intercept values become the $R_{C2}$ and $E_{C2}$ correction coefficients.

Correspondingly, the calibration method is automatically performed with 3 fixed energy values, thereby calculating the $E_{C1}$ and $E_{C2}$ correction coefficients. Voltage measurements, for both resistance and energy calculations, can be made at the heater cartridge connections, using a 4-wire method. The x, y, m, and b values are recorded in a settings file for both the resistance coefficients and the energy coefficients. The raw heater voltage and the current shunt resistor voltage are recorded in a data log file for measurement redundancy and future analysis. This data can also aid in the determination of the battery requirements for a battery powered vapor generator. Such a battery powered vapor generator can be utilized in an hand-held inhaler according to exemplary embodiments.

The new equations for calculating energy and resistance variations are as follows:

$$\text{Energy}_{k+1}=(((\text{Input1}*\text{Input2}*20*E_{C1})+E_{C2})/1000)+\text{Energy}_k \quad (12)$$

$$\text{Resistance}=((\text{Input1}/(\text{Input2}*20))*R_{C1})+R_{C2} \quad (13)$$

Input1=$V_{heater}$, the voltage drop across the heater. Input2=$V_{shunt}$, and is used to calculate the current through the heater: I=$V_{shunt}/R_{shunt}$. The value of $R_{shunt}$ is 0.050 ohms. While a shunt resistor with a different resistance can be used, a 0.050 ohm resistor is chosen to optimize the signal-to-noise ratio. Placing these values into the equations above results in, $$\text{Energy}_{k+1} = ((V_{heater} * V_{shunt} * 20 * E_{C1}) + E_{C2} * 0.001) + \text{Energy}_k \quad (14)$$

$$\text{Resistance} = (((V_{heater}/V_{shunt} * 20)) * R_{C1}) + R_{C2} \quad (15)$$

Calculating the correction coefficients for the energy/resistance control algorithm for controlling the vapor generator along a linear algorithm has the effect of averaging the coefficients along a line rather than at a single point, thereby providing more accurate control of the vapor generator by better accommodating variations in, or across a range of, energy and/or resistance.

While the invention has been described with reference to the foregoing embodiments, it will be apparent that various changes can be made to the instrument and/or method of use thereof. While the instrument has been described as useful for characterizing aerosols for inhalation or other uses such as toxicology studies, the instrument could be used for additional purposes such as applying coatings such as optical coatings to a substrate, making powders such as nanosize powders, delivering vaporized fuel to devices such as a microcombustor, delivering multiple feeds of volatilized fluids for chemical interaction thereof or other purpose, and the like.

What is claimed is:

1. A computer-based method for controlling a vapor generator, comprising:
    (a) receiving vapor generator control parameters;
    (b) directing the operation of a vapor generator for a fixed period, wherein the generator is controlled by the received control parameters;
    (c) storing the control parameters and operational data of the vapor generator as a control profile for the vapor generator;
    (d) repeating steps (b)–(c) for a predetermined number of iterations;
    (e) selecting a stored control profile; and
    (f) automatically controlling the operation of the vapor generator with the data of the selected control profile.

2. The method according to claim 1, wherein the control parameters are received by means of a user interface.

3. The method according to claim 1, wherein the control parameters include power range, power supply voltage, heater off time, heater delay time, start resistance value, resistance increment value, maximum power value, liquid material formulation, and pump flow rate.

4. The method according to claim 1, wherein the predetermined number of iterations is 3.

5. The method according to claim 1, wherein the operational data of the vapor generator includes the power level used to energize the vapor generator to achieve a targeted resistance value.

6. The method according to claim 1, wherein the stored control profiles can be either desirable or undesirable profiles for controlling the operation of the vapor generator.

7. The method according to claim 1, wherein automatically controlling the operation of the vapor generator includes automatically providing power to one or more heaters and initiating fluid delivery to the one or more heaters.

8. The method according to claim 7, wherein power can be shut off to the one or more heaters and fluid delivery can be stopped upon occurrence of a predetermined event.

9. The method according to claim 8, where the predetermined event can include one or more of: over resistance, over pressure, under energy, or over power.

10. The method according to claim 8, wherein an event log entry is created upon occurrence of the predetermined event.

11. The method according to claim 1, wherein step (b) includes pumping a liquid through a capillary sized flow passage and heating the flow passage such that the liquid forms a vapor which exits the flow passage and forms an aerosol in ambient air.

12. A computer-based method for controlling a vapor generator, comprising:
    selecting a profile for the operation of a vapor generator; and
    automatically directing the operation of the vapor generator based on the data of the selected profile, wherein the data of the selected profile includes:
        a voltage of a power supply of the vapor generator for directing power to a heater of the vapor generator;
        a power range for energizing the heater; and
        a target resistance for the heater.

13. The method according to claim 12, including automatically determining a minimal level of power sufficient to continuously measure resistance and energy without heating the heater.

14. The method according to claim 12, wherein the heater comprises a plurality of heaters.

15. The method according to claim 12, wherein the automatically directing includes pumping a liquid through a capillary sized flow passage and heating the flow passage such that the liquid forms a vapor which exits the flow passage and forms an aerosol in ambient air.

16. A computer-based method for controlling a vapor generator, comprising:
    calibrating the operation of a vapor generator with at least two precision resistances, wherein the power level required to energize at least one heater across each of the at least two resistances is recorded upon operation of the vapor generator for a fixed period of time;
    calculating a function based on the at least two precision resistances and the corresponding at least two recorded power levels;
    calculating the slope of the function as a first correction coefficient;
    calculating the intercept of the function on a y axis as a second correction coefficient; and
    automatically applying the first and second correction coefficients to software of a controller for directing the operation of the at least one heater of the vapor generator.

17. The method according to claim 16, wherein the first and second correction coefficients correct for variances in resistance within the vapor generator.

18. The method according to claim 16, wherein the first and second correction coefficients correct for variances in energy being sent to the heater of the vapor generator.

19. The method according to claim 16, wherein the software controls pumping a liquid through a capillary sized flow passage and controls the heater to heat the flow passage such that the liquid forms a vapor which exits the flow passage and forms an aerosol in ambient air.

20. The method according to claim 16, including calculating a polynomial function, based on at least three precision resistances and a corresponding at least three recorded energy levels, to compensate for non-linear behavior of the vapor generator.

21. The computer-based method according to claim 16, wherein the method includes:
  calibrating the operation of a vapor generator with at least three precision resistances, wherein the power level required to energize at least one heater across each of the at least three resistances is recorded upon operation of the vapor generator for a fixed period of time;
  calculating a linear function based on the at least three precision resistances and the corresponding at least three recorded power levels;
  calculating the slope of the linear function as a first correction coefficient;
  calculating the intercept of the linear function on a y axis as a second correction coefficient; and
  automatically applying the first and second correction coefficients to software of a controller for directing the operation of the at least one heater of the vapor generator.

22. A computer-based system for controlling a vapor generator, comprising:
  a controller configured to direct operation of a vapor generator;
  a user interface configured to receive control parameters for controlling the operation of the controller, including selection of a vapor generator profile;
  at least one heater powered by an energy source according to the selected vapor generator profile; and
  at least one pump directing a fluid material through the at least one heater, wherein the at least one heater is energized by the energy source such that the fluid material is vaporized by the heater.

23. The system according to claim 22, wherein the controller is configured to meet a plurality of resistance targets during a vapor generation run.

24. The system according to claim 22, wherein the at least one heater includes a capillary sized flow passage through which the fluid is pumped by the at least one pump, the flow passage having an outlet through which the vaporized fluid is ejected into ambient air so as to form an aerosol.

25. A computer-based system for controlling a vapor generator, comprising:
  a user interface module configured to receive control parameters for controlling the operation of the vapor generator;
  a profile module configured to automatically create one or more profiles for controlling the operation of the vapor generator based on the received control parameters, wherein the user interface module is further configured to select one or more of the created profiles; and
  a heater module configured to energize one or more heaters and to provide for fluid delivery to the one or more heaters based on one or more user-selected profiles.

26. The system according to claim 25, wherein each of the one or more heaters includes a capillary sized flow passage through which the fluid is pumped by a pump, the flow passage having an outlet through which vaporized fluid is ejected into ambient air so as to form an aerosol.

27. A vapor generator control system, comprising a computer system, said computer system including at least one of a software program for controlling a vapor generator, a user interface, a memory, and a profile module configured to receive user-specified control parameters and to create one or more profiles for controlling the operation of a vapor generator.

28. The system according to claim 27, wherein the vapor generator is an aerosol generator which generates timed delivery of an aerosol.

29. A system for controlling a vapor generator, comprising:
  means for receiving control parameters;
  means for creating one or more profiles for controlling a vapor generator;
  means for energizing one or more heaters according to the one or more profiles; and
  means for vaporizing a liquid material directed through the one or more heaters.

30. The system according to claim 29, wherein each of the one or more heaters includes a capillary sized flow passage through which the liquid is pumped by a pump, the flow passage having an outlet through which the vaporized liquid is ejected into ambient air so as to form an aerosol.

31. A computer-readable medium encoded with software for controlling the operation of a vapor generator, wherein the software is provided for:
  receiving vapor generator control parameters;
  directing the operation of a vapor generator for a fixed period, wherein the generator is controlled by the received control parameters;
  storing the control parameters and operational data of the vapor generator as a control profile for the vapor generator;
  selecting a stored control profile; and
  automatically controlling the operation of the vapor generator with the data of the selected control profile.

32. The computer-readable medium according to claim 31, wherein the vapor generator is an aerosol generator and the software directs intermittent or continuous operation of the aerosol generator.

33. A computer program, which, when executed by a computer, implements a vapor generator controller by performing the steps of:
  calibrating the operation of a vapor generator with at least two precision resistances, wherein the power level required to energize at least one heater across each of the at least two resistances is recorded upon operation of the vapor generator for a fixed period of time;
  calculating a function based on the at least two precision resistances and the corresponding at least two recorded power levels;
  calculating the slope of the function as a first correction coefficient;
  calculating the intercept of the function on a y axis as a second correction coefficient; and
  automatically applying the first and second correction coefficients to software of a controller for directing the operation of the at least one heater of the vapor generator.

34. The computer program according to claim 33, wherein the vapor generator is an aerosol generator and the software directs intermittent or continuous operation of the aerosol generator.

35. The method according to claim 33, including calculating a polynomial function, based on at least three precision resistances and a corresponding at least three recorded energy levels, to compensate for non-linear behavior of the vapor generator.

36. The computer program according to claim 33, wherein the computer program implements the vapor generator controller by further performing the steps of:
  calibrating the operation of a vapor generator with at least three precision resistances, wherein the power level required to energize at least one heater across each of the at least three resistances is recorded upon operation of the vapor generator for a fixed period of time;

calculating a linear function based on the at least three precision resistances and the corresponding at least three recorded power levels;

calculating the slope of the linear function as a first correction coefficient;

calculating the intercept of the linear function on a y axis as a second correction coefficient; and automatically applying the first and second correction coefficients to software of a controller for directing the operation of the at least one heater of the vapor generator.

* * * * *